US006902911B1

(12) United States Patent
Conklin et al.

(10) Patent No.: US 6,902,911 B1
(45) Date of Patent: Jun. 7, 2005

(54) HUMAN 2-19 PROTEIN HOMOLOGUE Z219C

(75) Inventors: Darrell C. Conklin, Seattle, WA (US); Hal Blumberg, Seattle, WA (US); Theresa A. Deisher, Seattle, WA (US)

(73) Assignee: ZymoGenetics, Inc., Seattle, WA (US)

( * ) Notice: Subject to any disclaimer, the term of this patent is extended or adjusted under 35 U.S.C. 154(b) by 0 days.

(21) Appl. No.: 09/186,342

(22) Filed: Nov. 4, 1998

Related U.S. Application Data

(60) Provisional application No. 60/066,157, filed on Nov. 19, 1997.

(51) Int. Cl.[7] .............................................. C12N 15/09
(52) U.S. Cl. ..................... 435/69.8; 435/69.7; 435/325; 435/252.3; 435/320.1; 536/23.4
(58) Field of Search ............................... 435/69.1, 325, 435/252.3, 254.4, 320.1, 69.7, 69.8; 536/23.5; 530/350

(56) References Cited

U.S. PATENT DOCUMENTS 5,733,748 A * 3/1998 Yu .............................. 435/70.1

FOREIGN PATENT DOCUMENTS

WO          96/39419      12/1996
WO          98/44133      10/1998

OTHER PUBLICATIONS

Genbank Accession No. AA297147, 1997.
Genbank Accession No. AA622758, 1997.
Genbank Accession No. AA563933, 1997.
Chen et al., Accession No. X55448, 1994.
Fu and Kamps, Mol. Cell. Biol. 17(3):1503–1512, 1997.
Ohno et al., DDBJ/EMBL Genbank, 1996: D87120.
Rosen, Public Database Accession No. T45883, 1997.
Bione et al., Public Database Accession No. XB7193, 1993.
Hillier, et al., The Wash U–Merck EST Project, 1995: EST287257.
Hillier, et al., The Wash U–Merck EST Project, 1995: EST442792.
Marra, et al., The Wash U–HHMI Mouse EST Project, 1996: EST561209.
Genbank Accession No. AA297147, 1997.
Genbank Accession No. AA622758, 1997.
Genbank Accession No. AA563933, 1997.
Chen et al., Accession No. X55448, 1994.
Fu and Kamps, Mol. Cell. Biol. 17(3):1503–1512, 1997.
Fu and Kamps, Public Database Accession No. U72677, 1997.
Rosen, Public Database Accession No. T45883, 1997.
Bione et al., Public Database Accession No. X87193, 1993.
Hillier, et al., The Wash U–Merck EST Project, 1995: EST639427.
Hillier, et al., The Wash U–Merck EST Project, 1995: EST639428.
Adams et al., The Institute for Genomic Research, 1997: EST939803.
Adams et al., The Institute for Genomic Research, 1997: EST938496.
Adams et al., The Institute for Genomic Research, 1997: EST938505.
Marra, et al., The Wash U–HHMI Mouse EST Project, 1996: EST1095557.
Strausberg, NCI, Cancer Genome Anatomy Project, 1997: EST1115306.
Marra, et al., The Wash U–HHMI Mouse EST Project, 1996: EST1156924.
Strausberg, NCI, Cancer Genome Anatomy Project, 1997: EST1159140.
Strausberg, NCI, Cancer Genome Anatomy Project, 1997: EST1189080.
Strausberg, NCI, Cancer Genome Anatomy Project, 1997: EST1214316.
Strausberg, NCI, Cancer Genome Anatomy Project, 1997: EST1202130.
Strausberg, NCI, Cancer Genome Anatomy Project, 1997: EST02887.
Strausberg, NCI, Cancer Genome Anatomy Project, 1997: EST32608.
Marra, et al., The Wash U–HHMi Mouse EST Project, 1996: EST1309962.
Strausberg, NCI, Cancer Genome Anatomy Project, 1997: EST1320502.
Strausberg, NCI, Cancer Genome Anatomy Project, 1997: EST1320314.
Strausberg, NCI, Cancer Genome Anatomy Project, 1997: EST1319864.
Strausberg, NCI, Cancer Genome Anatomy Project, 1997: EST1347144.
Strausberg, NCI, Cancer Genome Anatomy Project, 1997: EST1347052.

* cited by examiner

*Primary Examiner*—Lorraine M. Spector
(74) *Attorney, Agent, or Firm*—Jennifer K. Johnson; James M. Bogden

(57) ABSTRACT

The present invention relates to polynucleotide and polypeptide molecules for z219c, a novel member of the human 2-19 protein family. The polypeptides, and polynucleotides encoding them, may be used for detecting various human disease states and chromosomal abnormalities. The present invention also includes antibodies to the z219c polypeptides.

3 Claims, 1 Drawing Sheet

```
z219c-a_-r    MRVSGVLRLLALIFAIVTTWMFIRSYMS-FSMKTIRLPRWLASP----TK  45
MMU72677_1    --------------------------------------------------
219_HUMAN     MRLAGPLRIVVLVVSVGVTWIVVSILLGGPGSGFPRIQQLFTSPESSVTA  50
D87120_1_|    MRVAGAAKLVVAVAVFLLTFYVISQVFE-IKMDASLGNLFARSALDTAAR  49 z219c-a_-r    EIQVKKYKCGLIKPCPANYFAFKICSGAANVVGPTMCFEDRMIMSPVKNN  95
MMU72677_1    --------------------------------------------------
219_HUMAN     APRARKYKCGLPQPCPEEHLAFRVVSGAANVIGPKICLEDKMLMSSVKDN 100
D87120_1_|    STKPPRYKCGISKACPEKHFAFKMASGAANVVGPKICLEDNVLMSGVKNN  99 z219c-a_-r    VGRGLNIALVNGTTGAVLGQKAFDMYSGDVMHLVKFLKEIPGGALVLVAS 145
MMU72677_1    -------------TGQVMKKDSFDMYSGDPQLLLNFLTEIPDSTLVLVAS  37
219_HUMAN     VGRGLNIALVNGVSGELIEARAFDMWAGDVNDLLKFIRPLHEGTLVFVAS 150
D87120_1_|    VGRGINVALANGKTGEVLDTKYFDMWGGDVAPFIEFLKAIQDGTIVLMGT 149 z219c-a_-r    YDDPGTKMNDESRKLFSDLGSSYAKQLGFRDSWVFIGAKDLRGKSPFEQF 195
MMU72677_1    YDDPGTKMNDKIKTLFSNLGSSYAKQLGFRDSWVFVGAKDLKSKSPYEQF  87
219_HUMAN     YDDPATKMNEETRKLFSELGSRNAKELAFRDSWVFVGAKGVQNKSPFEQH 200
D87120_1_|    YDDGATKLNDEARRLIADLGSTSITNLGFRDNWVFCGGKGIKTKSPFEQH 199 z219c-a_-r    LKNSPDTNKYEGWPELLEMEGCMPPKPF--  223
MMU72677_1    LKNNPETNKYDGWPELLELEGCVPRKVM--  115
219_HUMAN     VKNSKHSNKYEGCPEALEMEGCIPRRSTAS  230
D87120_1_|    IKNNKDTNKYEGWPEVVEMEGCIPQKQD--  227
```

HUMAN 2-19 PROTEIN HOMOLOGUE Z219C

REFERENCE TO RELATED APPLICATIONS

This application is related to Provisional Application 60/066,157, filed on Nov. 19, 1997. Under 35 U.S.C. § 119(e)(1), this application claims benefit of said Provisional Application.

BACKGROUND OF THE INVENTION

Proliferation and differentiation of cells of multicellular organisms are controlled by hormones and polypeptide growth factors. These diffusable molecules allow cells to communicate with each other and act in concert to regulate cells and form organs, and to repair and regenerate damaged tissue. Examples of hormones and growth factors include the steroid hormones (e.g. estrogen, testosterone), parathyroid hormone, follicle stimulating hormone, the interleukins, platelet derived growth factor (PDGF), epidermal growth factor (EGF), granulocyte-macrophage colony stimulating factor (GM-CSF), erythropoietin (EPO) and calcitonin.

Hormones and growth factors influence cellular metabolism by binding to proteins. These proteins may be integral membrane proteins that are linked to signaling pathways within the cell, such as second messenger systems. Other classes of proteins that hormones and growth factors influence are soluble molecules, such as the transcription factors.

Thus, there is a continuing need to discover new hormones, growth factors and the like. The in vivo activities of these cytokines illustrates the enormous clinical potential of, and need for, other cytokines, cytokine agonists, and cytokine antagonists. The present invention addresses this need by providing such polypeptides for these and other uses that should be apparent to those skilled in the art from the teachings herein.

SUMMARY OF THE INVENTION

The present invention addresses this need by providing a novel polypeptide and related compositions and methods.

In one aspect, the present invention provides an isolated polynucleotide that encodes a polypeptide comprising a sequence of amino acid residues that is at least 90% identical to an amino acid sequence selected from the group consisting of: (a) the amino acid sequence as shown in SEQ ID NO:2 from amino acid number 23 (Phe), to amino acid number 223 (Phe); and (b) the amino acid sequence as shown in SEQ ID NO:2 from amino acid number 1 (Met), to amino acid number 223 (Phe). Within one embodiment, the isolated polynucleotide disclosed above consists of: (a) polynucleotide molecules comprising a nucleotide sequence as shown in SEQ ID NO:1 from nucleotide 285 to nucleotide 890; (b) polynucleotide molecules comprising a nucleotide sequence as shown in SEQ ID NO:1 from nucleotide 222 to nucleotide 890; and (c) polynucleotide molecules complementary to (a) or (b). Within another embodiment, the isolated polynucleotide disclosed above comprises nucleotide 1 to nucleotide 669 of SEQ ID NO:8. Within another embodiment, the isolated polynucleotide disclosed above consists of a sequence of amino acid residue that is at least 90% identical to an amino acid sequence as shown in SEQ ID NO:2 from amino acid number 23 (Phe), to amino acid number 223 (Phe). Within another embodiment, the isolated polynucleotide disclosed above consists of a sequence of amino acid residues as shown in SEQ ID NO:2 from amino acid number 23 (Phe), to amino acid number 223 (Phe).

Within another embodiment, the isolated polynucleotide disclosed above encodes a polypeptide that contains motifs 1, 2, 3, 4 and 5 spaced apart from N-terminus to C-terminus in a configuration M1-{25-26}-M2-{15}-M3-{11}-M4-{34-36}-M5.

Within a second aspect, the present invention provides an expression vector comprising the following operably linked elements: a transcription promoter; a DNA segment encoding a z219a polypeptide that is at least 90% identical to an amino acid sequence as shown in SEQ ID NO:2 from amino acid number 23 (Phe), to amino acid number 223 (Phe); and a transcription terminator, wherein the promoter is operably linked to the DNA segment, and the DNA segment is operably linked to the transcription terminator. Within one embodiment, the expression vector disclosed above further comprises a secretory signal sequence operably linked to the DNA segment.

Within a third aspect, the present invention provides a cultured cell into which has been introduced an expression vector as disclosed above, wherein the cell expresses the polypeptide encoded by the DNA segment.

Within a fourth aspect, the present invention provides a DNA construct encoding a fusion protein, the DNA construct comprising: a first DNA segment encoding a polypeptide that is at least 90% identical to a sequence of amino acid residues 1 (Met) through 21 (Met) of SEQ ID NO:2, and a second DNA segment encoding an additional polypeptide, wherein the first and second DNA segments are connected in-frame; and encode the fusion protein.

Within another aspect, the present invention provides an isolated peptide comprising a sequence of amino acid residues that is at least 90% identical to an amino acid sequence selected from the group consisting of: (a) polypeptide molecules comprising an amino acid sequence as shown in SEQ ID NO:2 from amino acid number 23 (Phe), to amino acid number 223 (Phe) of SEQ ID NO:2, and (b) polypeptide molecules comprising an amino acid sequence as shown in SEQ ID NO:2 from amino acid residue number 1 (Met) to amino acid residue number 223 (Phe). Within one embodiment, the isolate polypeptide disclosed above consists of a sequence of amino acid residues that is at least 90% identical to an amino acid sequence as shown in SEQ ID NO:2 from amino acid number 23 (Phe), to amino acid number 223 (Phe). Within another embodiment, the isolate polypeptide disclosed above is as shown in SEQ ID NO:2 from amino acid number 23 (Phe), to amino acid number 223 (Phe). Within another embodiment, the isolate polypeptide disclosed above encodes motifs 1, 2, 3, 4 and 5 spaced apart from N-terminus to C-terminus in a configuration M1-{25-26}-M2-{15}-M3-{11}-M4-{34-36}-M5.

Within another aspect, the present invention provides a method of producing a z219c polypeptide comprising: culturing a cell as disclosed above; and isolating the z219c polypeptide produced by the cell.

Within another aspect, the present invention provides a method of producing an antibody to z219c polypeptide comprising: inoculating an animal with a polypeptide selected from the group consisting of: (a) a polypeptide consisting of 9 to 210 amino acids, wherein the polypeptide is at least 90% identical to a contiguous sequence of amino acids in SEQ ID NO:2 from amino acid number 23 (Phe), to amino acid number 223 (Phe); (b) a polypeptide consisting of the amino acid sequence of SEQ ID NO:2 from amino acid number 22 (Phe) to amino acid number 88 (Ile); (c) a polypeptide consisting of the amino acid sequence of SEQ ID NO:2 from amino acid number 23 (Phe), to amino acid number 223 (Phe); (d) a polypeptide consisting of the amino acid sequence of SEQ ID NO:2 from amino acid number 51 (Lys) to amino acid number 124 (Asp); (e) a polypeptide consisting of the amino acid sequence of SEQ ID NO:2 from amino acid number 125 (Val) to amino acid number 202 (Thr); (f) a polypeptide consisting of the amino acid sequence of SEQ ID NO:2 from amino acid 203 (Phe) to amino acid number 223 (Phe); and wherein the polypeptide elicits an immune response in the animal to produce the antibody; and isolating the antibody from the animal.

In another aspect, the present invention provides an antibody produced by the method disclosed above, which binds to a z219c polypeptide. In one embodiment, the antibody disclosed above is a monoclonal antibody. In another aspect, the present invention provides an antibody which binds to a polypeptide as disclosed above.

In another aspect, the present invention provides a method of detecting, in a test sample, the presence of an antagonist of z219c protein activity, comprising: transfecting a z219c-responsive cell, with a reporter gene construct that is responsive to a z219c-stimulated cellular pathway; and producing a z219c polypeptide; and adding the z219c polypeptide to the cell, in the presence and absence of a test sample; and comparing levels of response to the z219c polypeptide, in the presence and absence of the test sample, by a biological or biochemical assay; and determining from the comparison, the presence of the antagonist of z219c activity in the test sample.

In another aspect, the present invention provides a method of detecting, in a test sample, the presence of an agonist of z219c protein activity, comprising: transfecting a z219c-responsive cell, with a reporter gene construct that is responsive to a z219c-stimulated cellular pathway; and adding a test sample; and comparing levels of response in the presence and absence of the test sample, by a biological or biochemical assay; and determining from the comparison, the presence of the agonist of z219c activity in the test sample.

BRIEF DESCRIPTION OF THE DRAWINGS

The FIGURE illustrates a multiple alignment of z219c (z219c.pep) (SEQ ID NO:2), murine EF-7 protein (MMU72677_1) (SEQ ID NO:17), human 2-19 protein (219_HUMAN) (SEQ ID NO:18), and D87120 (D87120_1_|) (SEQ ID NO:19).

DETAILED DESCRIPTION OF THE INVENTION

Prior to setting forth the invention in detail, it is helpful to the understanding thereof to define the following terms:

The term "affinity tag" is used herein to denote a polypeptide segment that can be attached to a second polypeptide to provide for purification or detection of the second polypeptide or provide sites for attachment of the second polypeptide to a substrate. In principal, any peptide or protein for which an antibody or other specific binding agent is available can be used as an affinity tag. Affinity tags include a poly-histidine tract, protein A (Nilsson et al., *EMBO J.* 4:1075, 1985; Nilsson et al., *Methods Enzymol.* 198:3, 1991), glutathione S transferase (Smith and Johnson, *Gene* 67:31, 1988), Glu—Glu affinity tag (Grussenmeyer et al., *Proc. Natl. Acad. Sci. USA* 82:7952–4, 1985), substance P, Flag™ peptide (Hopp et al., *Biotechnology* 6:1204–10, 1988), streptavidin binding peptide, or other antigenic epitope or binding domain. See, in general, Ford et al., *Protein Expression and Purification* 2: 95–107, 1991. DNAs encoding affinity tags are available from commercial suppliers (e.g., Pharmacia Biotech, Piscataway, N.J.).

The term "allelic variant" denotes any of two or more alternative forms of a gene occupying the same chromosomal locus. Allelic variation arises naturally through mutation, and may result in phenotypic polymorphism within populations. Gene mutations can be silent (no change in the encoded polypeptide) or may encode polypeptides having altered amino acid sequence. The term allelic variant is also used herein to denote a protein encoded by an allelic variant of a gene.

The terms "amino-terminal" and "carboxyl-terminal" are used herein to denote positions within polypeptides. Where the context allows, these terms are used with reference to a particular sequence or portion of a polypeptide to denote proximity or relative position. For example, a certain sequence positioned carboxyl-terminal to a reference sequence within a polypeptide is located proximal to the carboxyl terminus of the reference sequence, but is not necessarily at the carboxyl terminus of the complete polypeptide.

The term "complement/anti-complement pair" denotes non-identical moieties that form a non-covalently associated, stable pair under appropriate conditions. For instance, biotin and avidin (or streptavidin) are prototypical members of a complement/anti-complement pair. Other exemplary complement/anti-complement pairs include receptor/ligand pairs, antibody/antigen (or hapten or epitope) pairs, sense/antisense polynucleotide pairs, and the like. Where subsequent dissociation of the complement/anti-complement pair is desirable, the complement/anti-complement pair preferably has a binding affinity of $<10^9$ $M^{-1}$.

The term "complements of a polynucleotide molecule" denotes a polynucleotide molecule having a complementary base sequence and reverse orientation as compared to a reference sequence. For example, the sequence 5' ATG-CACGGG 3' is complementary to 5' CCCGTGCAT 3'.

The term "contig" denotes a polynucleotide that has a contiguous stretch of identical or complementary sequence to another polynucleotide. Contiguous sequences are said to "overlap" a given stretch of polynucleotide sequence either in their entirety or along a partial stretch of the polynucleotide. For example, representative contigs to the polynucleotide sequence 5'-ATGGCTTAGCTT-3' are 5'-TAGCTTgagtct-3' and 3'-gtcgacTACCGA-5'.

The term "degenerate nucleotide sequence" denotes a sequence of nucleotides that includes one or more degenerate codons (as compared to a reference polynucleotide molecule that encodes a polypeptide). Degenerate codons contain different triplets of nucleotides, but encode the same amino acid residue (i.e., GAU and GAC triplets each encode Asp).

The term "expression vector" denotes a DNA molecule, linear or circular, that comprises a segment encoding a polypeptide of interest operably linked to additional segments that provide for its transcription. Such additional segments may include promoter and terminator sequences, and may optionally include one or more origins of replication, one or more selectable markers, an enhancer, a polyadenylation signal, and the like. Expression vectors are generally derived from plasmid or viral DNA, or may contain elements of both.

The term "isolated", when applied to a polynucleotide, denotes that the polynucleotide has been removed from its natural genetic milieu and is thus free of other extraneous or unwanted coding sequences, and is in a form suitable for use within genetically engineered protein production systems. Such isolated molecules are those that are separated from their natural environment and include cDNA and genomic clones. Isolated DNA molecules of the present invention are free of other genes with which they are ordinarily associated, but may include naturally occurring 5' and 3' untranslated regions such as promoters and terminators. The identification of associated regions will be evident to one of ordinary skill in the art (see for example, Dynan and Tijan, *Nature* 316:774–78, 1985).

An "isolated" polypeptide or protein is a polypeptide or protein that is found in a condition other than its native environment, such as apart from blood and animal tissue. In a preferred form, the isolated polypeptide is substantially free of other polypeptides, particularly other polypeptides of animal origin. It is preferred to provide the polypeptides in a highly purified form, i.e., greater than 95% pure, more preferably greater than 99% pure. When used in this context, the term "isolated" does not exclude the presence of the same polypeptide in alternative physical forms, such as dimers or alternatively glycosylated or derivatized forms.

The term "operably linked", when referring to DNA segments, denotes that the segments are arranged so that they function in concert for their intended purposes, e.g., transcription initiates in the promoter and proceeds through the coding segment to the terminator.

The term "ortholog" denotes a polypeptide or protein obtained from one species that is the functional counterpart of a polypeptide or protein from a different species. Sequence differences among orthologs are the result of speciation.

"Paralogs" are distinct but structurally related proteins made by an organism. Paralogs are believed to arise through gene duplication. For example, α-globin, β-globin, and myoglobin are paralogs of each other.

A "polynucleotide" is a single- or double-stranded polymer of deoxyribonucleotide or ribonucleotide bases read from the 5' to the 3' end. Polynucleotides include RNA and DNA, and may be isolated from natural sources, synthesized in vitro, or prepared from a combination of natural and synthetic molecules. Sizes of polynucleotides are expressed as base pairs (abbreviated "bp"), nucleotides ("nt"), or kilobases ("kb"). Where the context allows, the latter two terms may describe polynucleotides that are single-stranded or double-stranded. When the term is applied to double-stranded molecules it is used to denote overall length and will be understood to be equivalent to the term "base pairs". It will be recognized by those skilled in the art that the two strands of a double-stranded polynucleotide may differ slightly in length and that the ends thereof may be staggered as a result of enzymatic cleavage; thus all nucleotides within a double-stranded polynucleotide molecule may not be paired.

A "polypeptide" is a polymer of amino acid residues joined by peptide bonds, whether produced naturally or synthetically. Polypeptides of less than about 10 amino acid residues are commonly referred to as "peptides".

The term "promoter" is used herein for its art-recognized meaning to denote a portion of a gene containing DNA sequences that provide for the binding of RNA polymerase and initiation of transcription. Promoter sequences are commonly, but not always, found in the 5' non-coding regions of genes.

A "protein" is a macromolecule comprising one or more polypeptide chains. A protein may also comprise non-peptidic components, such as carbohydrate groups. Carbohydrates and other non-peptidic substituents may be added to a protein by the cell in which the protein is produced, and will vary with the type of cell. Proteins are defined herein in terms of their amino acid backbone structures; substituents such as carbohydrate groups are generally not specified, but may be present nonetheless.

The term "receptor" denotes a cell-associated protein that binds to a bioactive molecule (i.e., a ligand) and mediates the effect of the ligand on the cell. In general, receptors can be membrane bound, cytosolic or nuclear; monomeric (e.g., thyroid stimulating hormone receptor, beta-adrenergic receptor) or multimeric (e.g., PDGF receptor, growth hormone receptor, IL-3 receptor, GM-CSF receptor, G-CSF receptor, erythropoietin receptor and IL-6 receptor). Membrane-bound receptors are characterized by a multi-domain structure comprising an extracellular ligand-binding domain and an intracellular effector domain that is typically involved in signal transduction. Most nuclear receptors also exhibit a multi-domain structure, including an amino-terminal, transactivating domain, a DNA binding domain and a ligand binding domain. Binding of ligand to receptor results in a conformational change in the receptor that causes an interaction between the effector domain and other molecule(s) in the cell. This interaction in turn leads to an alteration in the metabolism of the cell. Metabolic events that are linked to receptor-ligand interactions include gene transcription, phosphorylation, dephosphorylation, increases in cyclic AMP production, mobilization of cellular calcium, mobilization of membrane lipids, cell adhesion, hydrolysis of inositol lipids and hydrolysis of phospholipids.

The term "secretory signal sequence" denotes a DNA sequence that encodes a polypeptide (a "secretory peptide") that, as a component of a larger polypeptide, directs the larger polypeptide through a secretory pathway of a cell in which it is synthesized. The larger peptide is commonly cleaved to remove the secretory peptide during transit through the secretory pathway.

The term "splice variant" is used herein to denote alternative forms of RNA transcribed from a gene. Splice variation arises naturally through use of alternative splicing sites within a transcribed RNA molecule, or less commonly between separately transcribed RNA molecules, and may result in several mRNAs transcribed from the same gene. Splice variants may encode polypeptides having altered amino acid sequence. The term splice variant is also used herein to denote a protein encoded by a splice variant of an mRNA transcribed from a gene.

Molecular weights and lengths of polymers determined by imprecise analytical methods (e.g., gel electrophoresis) will be understood to be approximate values. When such a value is expressed as "about" X or "approximately" X, the stated value of X will be understood to be accurate to ±10%.

Teachings of all references cited herein are in their entirety incorporated by reference.

The present invention is based in part upon the discovery of a novel DNA sequence that encodes a polypeptide having homology to murine EF-7 protein, human 2-19 protein and human cancellous bone protein D87120. Analysis of the tissue distribution of the mRNA corresponding to this novel DNA showed that expression was highest in trachea, followed by strong expression levels in small intestine, stomach, colon and pancreas. The polypeptide has been designated z219c.

The novel z219c polypeptides of the present invention were initially identified by querying an EST database for proteins homologous to proteins having a secretory signal sequence. These proteins are characterized by an upstream methionine start site and a hydrophobic region of approximately 13 amino acids. Polypeptides meeting those search criteria were compared to an EST database to identify secreted proteins having homology to known ligands. A single EST sequence was discovered and predicted to code for part of a secreted protein and the full-length was isolated. The novel polypeptide encoded by the full length cDNA showed homology with the human 2-19 (Genbank accession No. X55448) and murine EF-7 protein family (Fu, X. and Kamps, M. P., *Mol. Cell. Biol.*, 17:1503–1511, 1997).

The full sequence of the z219c polypeptide was obtained from a single clone believed to contain it, wherein the clone was obtained from a gastrointestinal tissue library. Other libraries that can also be searched for such sequences include pancreas, trachea, stomach, colon, salivary gland, prostate, bone marrow, testis, mammary gland and the like.

The nucleotide sequence of full-length z219c is described in SEQ ID NO:1, and its deduced amino acid sequence is described in SEQ ID NO:2. The multiple alignment (FIGURE) revealed that z219c is a member of a family of proteins that are characterized by their signal sequence, predicted small size (15–40 kD), tissue-specific expression, certain novel motifs disclosed herein, glycosylation sites, and lack of long hydrophobic segments, suggesting a small secreted molecule with that is a new class of secreted cytokine-like molecules.

Analysis of the DNA encoding z219c polypeptide (SEQ ID NO:1) revealed an open reading frame encoding 223 amino acids (SEQ ID NO:2) comprising a predicted signal peptide of 21 amino acid residues (residue 1 (Met) to residue 21 (Met) of SEQ ID NO:2), and a mature polypeptide of 194 amino acids (residue 22 (Phe) to residue 223 (Phe) of SEQ ID NO:2). Multiple alignment of z219c with other members of the human 2-19 protein family revealed the following 3 regions of conserved amino acids (see FIGURE):

1) The first region, referred to hereinafter as "block1," corresponds to amino acid residues 51 (Lys) to amino acid residue 124 (Asp) of SEQ ID NO:2. Within block 1 there is one conserved motif referred to hereinafter as "motif 1" (SEQ ID NO:3; corresponding to amino acids 118 to 120 of SEQ ID NO:2).

2) The second region, referred to hereinafter as "block2," corresponds to amino acid residues 125 (Val) to amino acid residue 202 (Thr) of SEQ ID NO:2. Within block 2 there are three conserved motifs referred to hereinafter as "motif 2" (SEQ ID NO:4; corresponding to amino acids 146 to 148 of SEQ ID NO:2), "motif 3" (SEQ ID NO:5; corresponding to amino acids 164 to 166 of SEQ ID NO:2), and "motif 4" (SEQ ID NO:6; corresponding to amino acids 178 to 180 of SEQ ID NO:2).

3) The third region, referred to hereinafter as "block3," corresponds to amino acid residues 203 (Asn) to amino acid residue 223 (Phe) of SEQ ID NO:2. Within block 3 there is one conserved motif referred to hereinafter as "motif 5" (SEQ ID NO:7; corresponding to amino acids 215 to 217 of SEQ ID NO:2).

Motifs 1 through 5 are spaced apart from N-terminus to C-terminus in a configuration represented by the following:

M1-{25-26}-M2-{15}-M3-{11}-M4-{34-36}-M5, where M# denotes the specific motif disclosed above and {#} denotes the number of amino acids between the motifs.

The presence of transmembrane regions, and conserved and low variance motifs generally correlates with or defines important structural regions in proteins. Regions of low variance (e.g., hydrophobic clusters) are generally present in regions of structural importance (Sheppard, P. et al., supra.). Such regions of low variance often contain rare or infrequent amino acids, such as Tryptophan. The regions flanking and between such conserved and low variance motifs may be more variable, but are often functionally significant because they relate to or define important structures and activities such as binding domains, biological and enzymatic activity, signal transduction, cell—cell interaction, tissue localization domains and the like.

Moreover, z219c polypeptide has a predicted glycosylation site located at amino acid 198 (Asn) in SEQ ID NO:2. This predicted glycosylation site at amino acid 198 is conserved throughout the family. The corresponding polynucleotides encoding the z219c polypeptide regions, domains, motifs, residues and sequences described above are as shown in SEQ ID NO:1.

The highly conserved amino acids in motifs 1 through 5 of z219c can be used as a tool to identify new family members. For instance, reverse transcription-polymerase chain reaction (RT-PCR) can be used to amplify sequences encoding the conserved motifs from RNA obtained from a variety of tissue sources or cell lines. In particular, highly degenerate primers designed from the z219c sequences are useful for this purpose.

SEQ ID NO:8 is a degenerate polynucleotide sequence that encompasses all polynucleotides that encode the z219c polypeptide of SEQ ID NO:2 (amino acids 1–223). Thus, z219c polypeptide-encoding polynucleotides ranging from nucleotide 1 to nucleotide 669 of SEQ ID NO:8 are contemplated by the present invention. Also contemplated by the present invention are fragments and fusions as described herein with respect to SEQ ID NO:1 and SEQ ID NO:2, which are formed from analogous regions of SEQ ID NO:8. The symbols in SEQ ID NO:8 are summarized in Table 1 below.

TABLE 1

| Nucleotide | Resolutions | Complement | Resolutions |
| --- | --- | --- | --- |
| A | A | T | T |
| C | C | G | G |
| G | G | C | C |
| T | T | A | A |
| R | A\|G | Y | C\|T |
| Y | C\|T | R | A\|G |
| M | A\|C | K | G\|T |
| K | G\|T | M | A\|C |
| S | C\|G | S | C\|G |
| W | A\|T | W | A\|T |
| H | A\|C\|T | D | A\|G\|T |
| B | C\|G\|T | V | A\|C\|G |
| V | A\|C\|G | B | C\|G\|T |
| D | A\|G\|T | H | A\|C\|T |
| N | A\|C\|G\|T | N | A\|C\|G\|T |

The degenerate codons used in SEQ ID NO:8, encompassing all possible codons for a given amino acid, are set forth in Table 2 below.

TABLE 2

| Amino Acid | Letter | Codons | Degenerate Codon |
| --- | --- | --- | --- |
| Cys | C | TGC TGT | TGY |
| Ser | S | AGC AGT TCA TCC TCG TCT | WSN |

TABLE 2-continued

| Amino Acid | Letter | Codons | Degenerate Codon |
|---|---|---|---|
| Thr | T | ACA ACC ACG ACT | ACN |
| Pro | P | CCA CCC CCG CCT | CCN |
| Ala | A | GCA GCC GCG GCT | GCN |
| Gly | G | GGA GGC GGG GGT | GGN |
| Asn | N | AAC AAT | AAY |
| Asp | D | GAC GAT | GAY |
| Glu | E | GAA GAG | GAR |
| Gln | Q | CAA CAG | CAR |
| His | H | CAC CAT | CAY |
| Arg | R | AGA AGG CGA CGC CGG CGT | MGN |
| Lys | K | AAA AAG | AAR |
| Met | M | ATG | ATG |
| Ile | I | ATA ATC ATT | ATH |
| Leu | L | CTA CTC CTG CTT TTA TTG | YTN |
| Val | V | GTA GTC GTG GTT | GTN |
| Phe | F | TTC TTT | TTY |
| Tyr | Y | TAC TAT | TAY |
| Trp | W | TGG | TGG |
| Ter | — | TAA TAG TGA | TRR |
| Asn\|Asp | B | | RAY |
| Glu\|Gln | Z | | SAR |
| Any | X | | NNN |
| Gap | — | — | |

One of ordinary skill in the art will appreciate that some ambiguity is introduced in determining a degenerate codon, representative of all possible codons encoding each amino acid. For example, the degenerate codon for serine (WSN) can, in some circumstances, encode arginine (AGR), and the degenerate codon for arginine (MGN) can, in some circumstances, encode serine (AGY). A similar relationship exists between codons encoding phenylalanine and leucine. Thus, some polynucleotides encompassed by the degenerate sequence may encode variant amino acid sequences, but one of ordinary skill in the art can easily identify such variant sequences by reference to the amino acid sequence encoded by the polynucleotides of SEQ ID NO:8. Such variant sequences can be tested for functionality as discussed herein.

Within preferred embodiments of the invention the isolated polynucleotides will hybridize to similar sized regions of SEQ ID NO:1, or a sequence complementary thereto, under stringent conditions. In general, stringent conditions are selected to be about 5° C. lower than the thermal melting point ($T_m$) for the specific sequence at a defined ionic strength and pH. The $T_m$ is the temperature (under defined ionic strength and pH) at which 50% of the target sequence hybridizes to a perfectly matched probe. Suitable stringent hybridization conditions are equivalent to about a 5 h to overnight incubation at about 42° C. in a solution comprising: about 40–50% formamide, up to about 5×SSC, about 5× Denhardt's solution, up to about 10% dextran sulfate, and about 10–20 µg/ml denatured commercially-available carrier DNA; hybridization is then followed by washing filters in up to about 2×SSC. For example, a suitable wash stringency is equivalent to 0.1×SSC to 2×SSC, 0.1% SDS, at 55° C. to 65° C. Stringent hybridization and wash conditions depend on the length of the probe, reflected in the Tm, hybridization and wash solutions used, and are routinely determined empirically by one of skill in the art.

As previously noted, the isolated polynucleotides of the present invention include DNA and RNA. Methods for preparing DNA and RNA are well known in the art. In general, RNA is isolated from a tissue or cell that produces large amounts of z219c RNA. Such tissues and cells are identified by Northern blotting (Thomas, *Proc. Natl. Acad. Sci. USA* 77:5201, 1980), and include pancreas, small intestine or prostate although DNA can also be prepared using RNA from other tissues or cell lines or isolated as genomic DNA. Total RNA can be prepared using guanidinium isothiocyanate extraction followed by isolation by centrifugation in a CsCl gradient (Chirgwin et al., *Biochemistry* 18:52–94, 1979). Poly (A)$^+$ RNA is prepared from total RNA using the method of Aviv and Leder (*Proc. Natl. Acad. Sci. USA* 69:1408–1412, 1972). Complementary DNA (cDNA) is prepared from poly(A)$^+$ RNA using known methods. In the alternative, genomic DNA can be isolated. Polynucleotides encoding z219c, polypeptides are then identified and isolated by, for example, hybridization or PCR.

A full-length clone encoding z219c can be obtained by conventional cloning procedures. Complementary DNA (cDNA) clones are preferred, although for some applications (e.g., expression in transgenic animals) it may be preferable to use a genomic clone, or to modify a cDNA clone to include at least one genomic intron. Methods for preparing cDNA and genomic clones are well known and within the level of ordinary skill in the art, and include the use of the sequence disclosed herein, or sub-sequence thereof, for probing or priming a library. Expression libraries can be probed with antibodies to z219c, receptor fragments, or other specific binding partners.

The polynucleotides of the present invention can also be synthesized using DNA synthesis machines. Currently the method of choice is the phosphoramidite method. If chemically synthesized double stranded DNA is required for an application such as the synthesis of a gene or a gene fragment, then each complementary strand is made separately. The production of short polynucleotides (60 to 80 bp) is technically straightforward and can be accomplished by synthesizing the complementary strands and then annealing them. However, for producing longer polynucleotides (>300 bp), special strategies are usually employed, because the coupling efficiency of each cycle during chemical DNA synthesis is seldom 100%. To overcome this problem, synthetic genes (double-stranded) are assembled in modular form from single-stranded fragments that are from 20 to 100 nucleotides in length.

One method for building a synthetic gene requires the initial production of a set of overlapping, complementary oligonucleotides, each of which is between 20 to 60 nucleotides long. Each internal section of the gene has complementary 3' and 5' terminal extensions designed to base pair precisely with an adjacent section. Thus, after the gene is assembled, process is completed by sealing the nicks along the backbones of the two strands with T4 DNA ligase. In addition to the protein coding sequence, synthetic genes can be designed with terminal sequences that facilitate insertion into a restriction endonuclease site of a cloning vector.

An alternative way to prepare a full-length gene is to synthesize a specified set of overlapping oligonucleotides (40 to 100 nucleotides). After the 3' and 5' short overlapping complementary regions are annealed, large gaps still remain, but the short base-paired regions are both long enough and stable enough to hold the structure together. The gaps are filled and the DNA duplex is completed via enzymatic DNA synthesis by *E. coli* DNA polymerase I. After the enzymatic synthesis is completed, the nicks are sealed. Double-stranded constructs are sequentially linked to one another to form the entire gene sequence which is verified by DNA sequence analysis. See Glick and Pasternak, *Molecular Biotechnology, Principles & Applications of Recombinant DNA*, (ASM Press, Washington, D.C. 1994); Itakura et al., *Annu. Rev. Biochem.* 53: 323–56, 1984 and Climie et al., *Proc. Natl. Acad. Sci. USA* 87:633–7, 1990.

The present invention further provides counterpart polypeptides and polynucleotides from other species (orthologs). These species include, but are not limited to mammalian, avian, amphibian, reptile, fish, insect and other vertebrate and invertebrate species. Of particular interest are z219c polypeptides from other mammalian species, including murine, rat, porcine, ovine, bovine, canine, feline, equine, and other primate polypeptides. Orthologs of human z219c can be cloned using information and compositions provided by the present invention in combination with conventional cloning techniques. For example, a cDNA can be cloned using mRNA obtained from a tissue or cell type that expresses z219c as disclosed herein. Suitable sources of mRNA can be identified by probing Northern blots with probes designed from the sequences disclosed herein. A library is then prepared from mRNA of a positive tissue or cell line. A z219c-encoding cDNA can then be isolated by a variety of methods, such as by probing with a complete or partial human cDNA or with one or more sets of degenerate probes based on the disclosed sequences. A cDNA can also be cloned using the polymerase chain reaction, or PCR (Mullis, U.S. Pat. No. 4,683,202), using primers designed from the representative human z219c sequence disclosed herein. Within an additional method, the cDNA library can be used to transform or transfect host cells, and expression of the cDNA of interest can be detected with an antibody to z219c polypeptide. Similar techniques can also be applied to the isolation of genomic clones.

Those skilled in the art will recognize that the sequence disclosed in SEQ ID NO:1 represents a single allele of human z219c and that allelic variation and alternative splicing are expected to occur. Allelic variants of this sequence can be cloned by probing cDNA or genomic libraries from different individuals according to standard procedures. Allelic variants of the DNA sequence shown in SEQ ID NO:1, including those containing silent mutations and those in which mutations result in amino acid sequence changes, are within the scope of the present invention, as are proteins which are allelic variants of SEQ ID NO:2. cDNAs generated from alternatively spliced mRNAs, which retain the properties of the z219c polypeptide are included within the scope of the present invention, as are polypeptides encoded by such cDNAs and mRNAs. Allelic variants and splice variants of these sequences can be cloned by probing cDNA or genomic libraries from different individuals or tissues according to standard procedures known in the art. Variants of this sequence can be cloned by probing human cDNA libraries, e.g. a human pancreatic, prostate or small intestine cDNA library, according to standard procedures.

The present invention also provides isolated z219c polypeptides that are substantially homologous to the polypeptides of SEQ ID NO:2 and their orthologs. The term "substantially similar" is used herein to denote polypeptides having preferably at least 70%, more preferably at least 80%, sequence identity to the sequences shown in SEQ ID NO:2 of their orthologs or paralogs. Such polypeptides will more preferably be at least 90% identical, and most preferably 95% or more identical to SEQ ID NO:2 or its orthologs or paralogs. Percent sequence identity is determined by conventional methods. See, for example, Altschul et al., *Bull. Math. Bio.* 48: 603–616, 1986 and Henikoff and Henikoff, *Proc. Natl. Acad. Sci. USA* 89:10915–10919, 1992. Briefly, two amino acid sequences are aligned to optimize the alignment scores using a gap opening penalty of 10, a gap extension penalty of 1, and the "blosum 62" scoring matrix of Henikoff and Henikoff (ibid.) as shown in Table 3 (amino acids are indicated by the standard one-letter codes). The percent identity is then calculated as:

$$\frac{\text{Total number of identical matches} \times 100}{[\text{length of the longer sequence plus the number of gaps introduced into the longer sequence in order to align the two sequences}]}$$

TABLE 3

| | A | R | N | D | C | Q | E | G | H | I | L | K | M | F | P | S | T | W | Y | V |
|---|---|---|---|---|---|---|---|---|---|---|---|---|---|---|---|---|---|---|---|---|
| A | 4 | | | | | | | | | | | | | | | | | | | |
| R | -1 | 5 | | | | | | | | | | | | | | | | | | |
| N | -2 | 0 | 6 | | | | | | | | | | | | | | | | | |
| D | -2 | -2 | 1 | 6 | | | | | | | | | | | | | | | | |
| C | 0 | -3 | -3 | -3 | 9 | | | | | | | | | | | | | | | |
| Q | -1 | 1 | 0 | 0 | -3 | 5 | | | | | | | | | | | | | | |
| E | -1 | 0 | 0 | 2 | -4 | 2 | 5 | | | | | | | | | | | | | |
| G | 0 | -2 | 0 | -1 | -3 | -2 | -2 | 6 | | | | | | | | | | | | |
| H | -2 | 0 | 1 | -1 | -3 | 0 | 0 | -2 | 8 | | | | | | | | | | | |
| I | -1 | -3 | -3 | -3 | -1 | -3 | -3 | -4 | -3 | 4 | | | | | | | | | | |
| L | -1 | -2 | -3 | -4 | -1 | -2 | -3 | -4 | -3 | 2 | 4 | | | | | | | | | |
| K | -1 | 2 | 0 | -1 | -3 | 1 | 1 | -2 | -1 | -3 | -2 | 5 | | | | | | | | |
| M | -1 | -1 | -2 | -3 | -1 | 0 | -2 | -3 | -2 | 1 | 2 | -1 | 5 | | | | | | | |
| F | -2 | -3 | -3 | -3 | -2 | -3 | -3 | -3 | -1 | 0 | 0 | -3 | 0 | 6 | | | | | | |
| P | -1 | -2 | -2 | -1 | -3 | -1 | -1 | -2 | -2 | -3 | -3 | -1 | -2 | -4 | 7 | | | | | |
| S | 1 | -1 | 1 | 0 | -1 | 0 | 0 | 0 | -1 | -2 | -2 | 0 | -1 | -2 | -1 | 4 | | | | |
| T | 0 | -1 | 0 | -1 | -1 | -1 | -1 | -2 | -2 | -1 | -1 | -1 | -1 | -2 | -1 | 1 | 5 | | | |
| W | -3 | -3 | -4 | -4 | -2 | -2 | -3 | -2 | -2 | -3 | -2 | -3 | -1 | 1 | -4 | -3 | -2 | 11 | | |
| Y | -2 | -2 | -2 | -3 | -2 | -1 | -2 | -3 | 2 | -1 | -1 | -2 | -1 | 3 | -3 | -2 | -2 | 2 | 7 | |
| V | 0 | -3 | -3 | -3 | -1 | -2 | -2 | -3 | -3 | 3 | 1 | -2 | 1 | -1 | -2 | -2 | 0 | -3 | -1 | 4 |

Sequence identity of polynucleotide molecules is determined by similar methods using a ratio as disclosed above.

Variant z219c polypeptides or substantially homologous z219c polypeptides are characterized as having one or more amino acid substitutions, deletions or additions. These changes are preferably of a minor nature, that is conservative amino acid substitutions (see Table 4) and other substitutions that do not significantly affect the folding or activity of the polypeptide; small deletions, typically of one to about 30 amino acids; and small amino- or carboxyl-terminal extensions, such as an amino-terminal methionine residue, a linker peptide of up to about 20–25 residues, or an extension that facilitates purification (an affinity tag), such as a polyhistidine tract, protein A (Nilsson et al., *EMBO J.* 4: 1075, 1985; Nilsson et al., *Methods Enzymol.* 198:3, 1991), glutathione S transferase (Smith and Johnson, *Gene* 67:31, 1988), maltose binding protein (Kellerman and Ferenci, *Methods Enzymol.* 90:459–463, 1982; Guan et al., *Gene* 67:21–30, 1987), thioredoxin, ubiquitin, cellulose binding protein, T7 polymerase, or other antigenic epitope or binding domain. See, in general Ford et al., *Protein Expression and Purification* 2: 95–107, 1991. DNAs encoding affinity tags are available from commercial suppliers (e.g., Pharmacia Biotech, Piscataway, N.J.; New England Biolabs, Beverly, Mass.). The present invention thus includes polypeptides of from about 195 to about 250 amino acid residues that comprise a sequence that is at least 80%, preferably at least 90%, and more preferably 95% or more identical to the corresponding region of SEQ ID NO:2. Polypeptides comprising affinity tags can further comprise a proteolytic cleavage site between the z219c polypeptide and the affinity tag. Preferred such sites include thrombin cleavage sites and factor Xa cleavage sites.

TABLE 4

Conservative amino acid substitutions

| | |
|---|---|
| Basic: | arginine |
| | lysine |
| | histidine |
| Acidic: | glutamic acid |
| | aspartic acid |
| Polar: | glutamine |
| | asparagine |
| Hydrophobic: | leucine |
| | isoleucine |
| | valine |
| Aromatic: | phenylalanine |
| | tryptophan |
| | tyrosine |
| Small: | glycine |
| | alanine |
| | serine |
| | threonine |
| | methionine |

The present invention further provides a variety of other polypeptide fusions and related multimeric proteins comprising one or more polypeptide fusions. For example, a z219c polypeptide can be prepared as a fusion to a dimerizing protein as disclosed in U.S. Pat. Nos. 5,155,027 and 5,567,584. Preferred dimerizing proteins in this regard include immunoglobulin constant region domains. Immunoglobulin z219c polypeptide fusions can be expressed in genetically engineered cells to produce a variety of multimeric z219c analogs. Auxiliary domains can be fused to z219c polypeptides to target them to specific cells, tissues, or macromolecules (e.g., collagen). For example, a z219c polypeptide or protein could be targeted to a predetermined cell type by fusing a z219c polypeptide to a ligand that specifically binds to a receptor on the surface of the target cell. In this way, polypeptides and proteins can be targeted for therapeutic or diagnostic purposes. A z219c polypeptide can be fused to two or more moieties, such as an affinity tag for purification and a targeting domain. Polypeptide fusions can also comprise one or more cleavage sites, particularly between domains. See, Tuan et al., *Connective Tissue Research* 34:1–9, 1996.

The proteins of the present invention can also comprise non-naturally occurring amino acid residues. Non-naturally occurring amino acids include, without limitation, trans-3-methylproline, 2,4-methanoproline, cis-4-hydroxyproline, trans-4-hydroxyproline, N-methylglycine, allo-threonine, methylthreonine, hydroxyethylcysteine, hydroxyethylhomocysteine, nitroglutamine, homoglutamine, pipecolic acid, thiazolidine carboxylic acid, dehydroproline, 3- and 4-methylproline, 3,3-dimethylproline, tert-leucine, norvaline, 2-azaphenylalanine, 3-azaphenylalanine, 4-azaphenylalanine, and 4-fluorophenylalanine.

Several methods are known in the art for incorporating non-naturally occurring amino acid residues into proteins. For example, an in vitro system can be employed wherein nonsense mutations are suppressed using chemically aminoacylated suppressor tRNAs. Methods for synthesizing amino acids and aminoacylating tRNA are known in the art. Transcription and translation of plasmids containing nonsense mutations is carried out in a cell-free system comprising an *E. coli* S30 extract and commercially available enzymes and other reagents. Proteins are purified by chromatography. See, for example, Robertson et al., *J. Am. Chem. Soc.* 113:2722, 1991; Ellman et al., *Methods Enzymol.* 202:301, 1991; Chung et al., *Science* 259:806–9, 1993; and Chung et al., *Proc. Natl. Acad. Sci. USA* 90:10145–9, 1993). In a second method, translation is carried out in *Xenopus* oocytes by microinjection of mutated mRNA and chemically aminoacylated suppressor tRNAs (Turcatti et al., *J. Biol. Chem.* 271:19991–8, 1996). Within a third method, *E. coli* cells are cultured in the absence of a natural amino acid that is to be replaced (e.g., phenylalanine) and in the presence of the desired non-naturally occurring amino acid(s) (e.g., 2-azaphenylalanine, 3-azaphenylalanine, 4-azaphenylalanine, or 4-fluorophenylalanine). The non-naturally occurring amino acid is incorporated into the protein in place of its natural counterpart. See, Koide et al., *Biochem.* 33:7470–6, 1994. Naturally occurring amino acid residues can be converted to non-naturally occurring species by in vitro chemical modification. Chemical modification can be combined with site-directed mutagenesis to further expand the range of substitutions (Wynn and Richards, *Protein Sci.* 2:395–403, 1993). A limited number of non-conservative amino acids, amino acids that are not encoded by the genetic code, and unnatural amino acids may be substituted for z219c amino acids residues.

Essential amino acids in the z219c polypeptides of the present invention can be identified according to procedures known in the art, such as site-directed mutagenesis or alanine-scanning mutagenesis (Cunningham and Wells, *Science* 244: 1081–1085, 1989; Bass et al., *Proc. Natl. Acad. Sci. USA* 88:4498–502, 1991). In the latter technique, single alanine mutations are introduced at every residue in the molecule, and the resultant mutant molecules are tested for biological or biochemical activity (e.g., in situ localization or expression of z219c; secretion followed by detection by antibodies; or activity measured by a signal transduction type assay) as disclosed below to identify amino acid residues that are critical to the activity of the molecule. See also, Hilton et al., *J. Biol. Chem.* 271:4699–4708, 1996. Sites of ligand-receptor or other biological interaction can also be determined by physical analysis of structure, as determined by such techniques as nuclear magnetic resonance, crystallography, electron diffraction or photoaffinity labeling, in conjunction with mutation of putative contact site amino acids. See, for example, de Vos et al., *Science* 255:306–312, 1992; Smith et al., *J. Mol. Biol.* 224:899–904, 1992; Wlodaver et al., *FEBS Lett.* 309:59–64, 1992. The identities of essential amino acids can also be inferred from analysis of homologies with related family members.

Multiple amino acid substitutions can be made and tested using known methods of mutagenesis and screening, such as those disclosed by Reidhaar-Olson and Sauer (*Science* 241:53–57, 1988) or Bowie and Sauer (*Proc. Natl. Acad.*

Sci. USA 86:2152–2156, 1989). Briefly, these authors disclose methods for simultaneously randomizing two or more positions in a polypeptide, selecting for functional polypeptide, and then sequencing the mutagenized polypeptides to determine the spectrum of allowable substitutions at each position. Other methods that can be used include phage display (e.g., Lowman et al., *Biochem.* 30:10832–10837, 1991; Ladner et al., U.S. Pat. No. 5,223,409; Huse, WIPO Publication WO 92/06204) and region-directed mutagenesis (Derbyshire et al., *Gene* 46:145, 1986; Ner et al., *DNA* 7:127, 1988).

Variants of the disclosed z219c DNA and polypeptide sequences can be generated through DNA shuffling as disclosed by Stemmer, *Nature* 370:389–91, 1994, Stemmer, *Proc. Natl. Acad. Sci. USA* 91:10747–51, 1994 and WIPO Publication WO 97/20078. Briefly, variant DNAs are generated by in vitro homologous recombination by random fragmentation of a parent DNA followed by reassembly using PCR, resulting in randomly introduced point mutations. This technique can be modified by using a family of parent DNAs, such as allelic variants or DNAs from different species, to introduce additional variability into the process. Selection or screening for the desired activity, followed by additional iterations of mutagenesis and assay provides for rapid "evolution" of sequences by selecting for desirable mutations while simultaneously selecting against detrimental changes.

Mutagenesis methods as disclosed herein can be combined with high-throughput, automated screening methods to detect activity of cloned, mutagenized polypeptides in host cells. Mutagenized DNA molecules that encode active polypeptides (e.g., secreted and detected by antibodies; or measured by a signal transduction type assay) can be recovered from the host cells and rapidly sequenced using modern equipment. These methods allow the rapid determination of the importance of individual amino acid residues in a polypeptide of interest, and can be applied to polypeptides of unknown structure.

Using the methods discussed herein, one of ordinary skill in the art can identify and/or prepare a variety of polypeptides that are substantially similar to SEQ ID NO:2 or allelic variants thereof and retain the properties of the wild-type protein. For example, using the methods described above, one could identify a receptor binding domain on z219c; an extracellular ligand-binding domain of a receptor for z219c; heterodimeric and homodimeric binding domains; other functional or structural domains; affinity tags; or other domains important for protein-protein interactions or signal transduction. Such polypeptides may also include additional polypeptide segments as generally disclosed above.

For any z219c polypeptide, including variants and fusion proteins, one of ordinary skill in the art can readily generate a fully degenerate polynucleotide sequence encoding that variant using the information set forth in Tables 1 and 2 above.

The polypeptides of the present invention, including full-length polypeptides, biologically active fragments, and fusion polypeptides, can be produced in genetically engineered host cells according to conventional techniques. Suitable host cells are those cell types that can be transformed or transfected with exogenous DNA and grown in culture, and include bacteria, fungal cells, and cultured higher eukaryotic cells. Eukaryotic cells, particularly cultured cells of multicellular organisms, are preferred. Techniques for manipulating cloned DNA molecules and introducing exogenous DNA into a variety of host cells are disclosed by Sambrook et al., *Molecular Cloning: A Laboratory Manual,* 2nd ed., Cold Spring Harbor Laboratory Press, Cold Spring Harbor, N.Y., 1989, and Ausubel et al., eds., *Current Protocols in Molecular Biology,* John Wiley and Sons, Inc., NY, 1987.

In general, a DNA sequence encoding a z219c polypeptide of the present invention is operably linked to other genetic elements required for its expression, generally including a transcription promoter and terminator within an expression vector. The vector will also commonly contain one or more selectable markers and one or more origins of replications, although those skilled in the art will recognize that within certain systems selectable markers may be provided on separate vectors, and replication of the exogenous DNA may be provided by integration into the host cell genome. Selection of promoters, terminators, selectable markers, vectors and other elements is a matter of routine design within the level of ordinary skill in the art. Many such elements are described in the literature and are available through commercial suppliers.

To direct a z219c polypeptide into the secretory pathway of a host cell, a secretory signal sequence (also known as a leader sequence, prepro sequence or pre sequence) is provided in the expression vector. The secretory signal sequence may be that of the z219c polypeptide, or may be derived from another secreted protein (e.g., t-PA) or synthesized de novo. The secretory signal sequence is operably linked to the z219c DNA sequence, i.e., the two sequences are joined in the correct reading frame and positioned to direct the newly synthesized polypeptide into the secretory pathway of the host cell. Secretory signal sequences are commonly positioned 5' to the DNA sequence encoding the polypeptide of interest, although certain secretory signal sequences may be positioned elsewhere in the DNA sequence of interest (see, e.g., Welch et al., U.S. Pat. No. 5,037,743; Holland et al., U.S. Pat. No. 5,143,830).

Alternatively, the signal sequence contained in the polypeptides of the present invention is used to direct other polypeptides into the secretory pathway. The present invention provides for such signal fusion polypeptides. A DNA construct can be made wherein a signal sequence disclosed in SEQ ID NO:2 (amino acids 1 through 21 of SEQ ID NO:2), can be operably linked to another polypeptide using methods known in the art and disclosed herein. The secretory signal sequence contained in the fusion polypeptides of the present invention is preferably fused amino-terminally to an additional peptide to direct the additional peptide into the secretory pathway. Such constructs have numerous applications known in the art. For example, these novel secretory signal sequence fusion constructs can direct the secretion of an active component of a normally non-secreted protein. Such fusions may be used in vivo or in vitro to direct peptides through the secretory pathway.

Cultured mammalian cells are suitable hosts within the present invention. Methods for introducing exogenous DNA into mammalian host cells include calcium phosphate-mediated transfection (Wigler et al., *Cell* 14:725, 1978; Corsaro and Pearson, *Somatic Cell Genetics* 7:603, 1981: Graham and Van der Eb, *Virology,* 52:456, 1973), electroporation (Neumann et al., *EMBO J.* 1:841–845, 1982), DEAE-dextran mediated transfection (Ausbel et al., ibid.), and liposome-mediated transfection (Hawley-Nelson et al., *Focus* 15:73, 1993; Ciccarone et al., *Focus* 15:80, 1993), and viral vectors (A. Miller and G. Rosman, *BioTechniques* 7:980–90, 1989; Q. Wang and M. Finer, *Nature Med.* 2:714–16, 1996). The production of recombinant polypeptides in cultured mammalian cells is disclosed, for example, by Levinson et al., U.S. Pat. No. 4,713,339; Hagan et al., U.S. Pat. No. 4,784,950; Palmiter et al., U.S. Pat. No. 4,579,821; and Ringold, U.S. Pat. No. 4,656,134. Suitable cultured mammalian cells include the COS-1 (ATCC No. CRL 1650), COS-7 (ATCC No. CRL 1651), BHK (ATCC No. CRL 1632), BHK 570 (ATCC No. CRL 10314), 293 (ATCC No. CRL 1573; Graham et al., *J. Gen. Virol.* 36:59–72, 1977) and Chinese hamster ovary (e.g., CHO-K1; ATCC No. CCL 61) cell lines. Additional suitable cell lines are known in the art and available from public depositories such as the American Type Culture Collection, Manassas, Va. In general, strong transcription promoters are preferred, such as promoters from SV-40 or cytomegalovirus (CMV). See, e.g., U.S. Pat. No. 4,956,288. Other suitable promoters include those from metallothionein genes (U.S. Pat. Nos. 4,579,821 and 4,601,978) and the adenovirus major late promoter.

Drug selection is generally used to select for cultured mammalian cells into which foreign DNA has been inserted. Such cells are commonly referred to as "transfectants." Cells that have been cultured in the presence of the selective agent and are able to pass the gene of interest to their progeny are referred to as "stable transfectants." A preferred selectable marker is a gene encoding resistance to the antibiotic neomycin. Selection is carried out in the presence of a neomycin-type drug, such as G-418 or the like. Selection systems can also be used to increase the expression level of the gene of interest, a process referred to as "amplification." Amplification is carried out by culturing transfectants in the presence of a low level of the selective agent and then increasing the amount of selective agent to select for cells that produce high levels of the products of the introduced genes. A preferred amplifiable selectable marker is dihydrofolate reductase, which confers resistance to methotrexate. Other drug resistance genes (e.g., hygromycin resistance, multi-drug resistance, puromycin acetyltransferase) can also be used. Alternative markers that introduce an altered phenotype, such as green fluorescent protein, or cell surface proteins such as CD4, CD8, Class I MHC, and placental alkaline phosphatase may be used to sort transfected cells from untransfected cells by such means as FACS sorting or magnetic bead separation technology.

Other higher eukaryotic cells can also be used as hosts, including plant cells, insect cells and avian cells. The use of *Agrobacterium rhizogenes* as a vector for expressing genes in plant cells has been reviewed by Sinkar et al., *J. Biosci. (Bangalore)* 11:47–58, 1987 and WIPO publication WO 94/06463. Transformation of insect cells and production of foreign polypeptides therein is disclosed by Guarino et al., U.S. Pat. No. 5,162,222; Bang et al., U.S. Pat. No. 4,775,624; and WIPO publication WO 94/06463. The use of *Agrobacterium rhizogenes* as a vector for expressing genes in plant cells has been reviewed by Sinkar et al., *J. Biosci. (Bangalore)* 11:47–58, 1987.

Fungal cells, including yeast cells, and particularly cells of the genus Saccharomyces, can also be used within the present invention, such as for producing z219c fragments or polypeptide fusions. Methods for Insect cells can be infected with recombinant baculovirus, commonly derived from *Autographa californica* nuclear polyhedrosis virus (AcNPV). See, King, L. A. and Possee, R. D., *The Baculovirus Expression System: A Laboratory Guide,* London, Chapman & Hall; O'Reilly, D. R. et al., *Baculovirus Expression Vectors: A Laboratory Manual,* New York, Oxford University Press., 1994; and, Richardson, C. D., Ed., *Baculovirus Expression Protocols, Methods in Molecular Biology,* Totows, N.J., Humana Press, 1995. A second method of making recombinant z219c baculovirus utilizes a transposon-based system described by Luckow (Luckow, V. A., et al., *J Virol* 67:4566–79, 1993). This system, which utilizes transfer vectors, is sold in the Bac-to-Bac™ kit (Life Technologies, Rockville, Md.). This system utilizes a transfer vector, pFastBacl™ (Life Technologies) containing a Tn7 transposon to move the DNA encoding the z219c polypeptide into a baculovirus genome maintained in *E. coli* as a large plasmid called a "bacmid." See, Hill-Perkins, M. S. and Possee, R. D., *J Gen Virol* 71:971–6, 1990; Bonning, B. C. et al., *J Gen Virol* 75:1551–6; 1994; and, Chazenbalk, G. D., and Rapoport, B., *J Biol Chem* 270:1543–9, 1995. In addition, transfer vectors can include an in-frame fusion with DNA encoding an epitope tag at the C- or N-terminus of the expressed z219c polypeptide, for example, a Glu-Glu epitope tag (Grussenmeyer, T. et al., *Proc. Natl. Acad. Sci.* 82:7952–4, 1985). Using a technique known in the art, a transfer vector containing z219c is transformed into *E. coli,* and screened for bacmids which contain an interrupted lacZ gene indicative of recombinant baculovirus. The bacmid DNA containing the recombinant baculovirus genome is isolated, using common techniques, and used to transfect *Spodoptera frugiperda* cells, e.g., Sf9 cells. Recombinant virus that expresses z219c is subsequently produced. Recombinant viral stocks are made by methods commonly used the art.

The recombinant virus is used to infect host cells, typically a cell line derived from the fall armyworm, *Spodoptera frugiperda*. See, in general, Glick and Pasternak, *Molecular Biotechnology: Principles and Applications of Recombinant DNA, ASM Press, Washington, D.C.,* 1994. Another suitable cell line is the High FiveO™ cell line (Invitrogen) derived from *Trichoplusia ni* (U.S. Pat. No. 5,300,435). Commercially available serum-free media are used to grow and maintain the cells. Suitable media are Sf900 II™ (Life Technologies) or ESF 921™ (Expression Systems) for the Sf9 cells; and Ex-cellO405™ (JRH Biosciences, Lenexa, Kans.) or Express FiveO™ (Life Technologies) for the *T. ni* cells. The cells are grown up from an inoculation density of approximately $2–5\times10^5$ cells to a density of $1–2\times10^6$ cells at which time a recombinant viral stock is added at a multiplicity of infection (MOI) of 0.1 to 10, more typically near 3. Procedures used are generally described in available laboratory manuals (King, L. A. and Possee, R. D., ibid.; O'Reilly, D. R. et al., ibid.; Richardson, C. D., ibid.). Subsequent purification of the z219c polypeptide from the supernatant can be achieved using methods described herein.

Fungal cells, including yeast cells, can also be used within the present invention. Yeast species of particular interest in this regard include *Saccharomyces cerevisiae, Pichia pastoris,* and *Pichia methanolica*. Methods for transforming *S. cerevisiae* cells with exogenous DNA and producing recombinant polypeptides therefrom are disclosed by, for example, Kawasaki, U.S. Pat. No. 4,599,311; Kawasaki et al., U.S. Pat. No. 4,931,373; Brake, U.S. Pat. No. 4,870,008; Welch et al., U.S. Pat. No. 5,037,743; and Murray et al., U.S. Pat. No. 4,845,075. Transformed cells are selected by phenotype determined by the selectable marker, commonly drug resistance or the ability to grow in the absence of a particular nutrient (e.g., leucine). A preferred vector system for use in *Saccharomyces cerevisiae* is the POT1 vector system disclosed by Kawasaki et al. (U.S. Pat. No. 4,931,373), which allows transformed cells to be selected by growth in glucose-containing media. Suitable promoters and terminators for use in yeast include those from glycolytic enzyme genes (see, e.g., Kawasaki, U.S. Pat. No. 4,599,311; Kingsman et al., U.S. Pat. No. 4,615,974; and Bitter, U.S. Pat. No.

4,977,092) and alcohol dehydrogenase genes. See also U.S. Pat. Nos. 4,990,446; 5,063,154; 5,139,936 and 4,661,454. Transformation systems for other yeasts, including *Hansenula polymorpha, Schizosaccharomyces pombe, Kluyveromyces lactis, Kluyveromyces fragilis, Ustilago maydis, Pichia pastoris, Pichia methanolica, Pichia guillermondii* and *Candida maltosa* are known in the art. See, for example, Gleeson et al., *J. Gen. Microbiol.* 132:3459–3465, 1986 and Cregg, U.S. Pat. No. 4,882,279. Aspergillus cells may be utilized according to the methods of McKnight et al., U.S. Pat. No. 4,935,349. Methods for transforming *Acremonium chrysogenum* are disclosed by Sumino et al., U.S. Pat. No. 5,162,228. Methods for transforming Neurospora are disclosed by Lambowitz, U.S. Pat. No. 4,486,533.

The use of *Pichia methanolica* as host for the production of recombinant proteins is disclosed in WIPO Publications WO 97/17450, WO 97/17451, WO 98/02536, and WO 98/02565. DNA molecules for use in transforming *P. methanolica* are be prepared as double-stranded, circular pladmids, which are preferably linearized prior to transformation. For polypeptide production in *P. methanolica*, it is preferred that the promoter and terminator in the plasmid be that of a *P. methanolica* gene, such as a *P. methanolica* alcohol utilization gene (AUG1 or AUG2). Other useful promoters include those of the dihydroxyacetone synthase (DHAS), formate dehydrogenase (FMD), and catalase (CAT) genes. To facilitate integration of the DNA into the host chromosome, it is preferred to have the entire expression segment of the plasmid flanked at both ends by host DNA sequences. A preferred selectable marker for use in *Pichia methanolica* is a *P. methanolica* ADE2 gene, which encodes phosphoribosyl-5-aminoimidazole carboxylase (AIRC; EC 4.1.1.21), which allows ade2 host cells to grow in the absence of adenine. For large-scale, industrial processes where it is desirable to minimize the use of methanol, it is preferred to use host cells in which both methanol utilization genes (AUG1 and AUG2) are deleted. For production of secreted proteins, host cells deficient in vacuolar protease genes (PEP4 and PRB1) are preferred. Electroporation is used to facilitate the introduction of a plasmid containing DNA encoding a polypeptide of interest into *P. methanolica* cells. It is preferred to transform *P. methanolica* cells by electroporation using an exponentially decaying, pulsed electric field having a field strength of from 2.5 to 4.5 kV/cm, preferably about 3.75 kV/cm, and a time constant (t) of from 1 to 40 milliseconds, most preferably about 20 milliseconds.

Transformed or transfected host cells are cultured according to conventional procedures in a culture medium containing nutrients and other components required for the growth of the chosen host cells. A variety of suitable media, including defined media and complex media, are known in the art and generally include a carbon source, a nitrogen source, essential amino acids, vitamins and minerals. Media may also contain such components as growth factors or serum, as required. The growth medium will generally select for cells containing the exogenously added DNA by, for example, drug selection or deficiency in an essential nutrient which is completed by the selectable marker carried on the expression vector or co-transfected into the host cell. *P. methanolica* cells are cultured in a medium comprising adequate sources of carbon, nitrogen and trace nutrients at a temperature of about 25° C. to 35° C. Liquid cultures are provided with sufficient aeration by conventional means, such as shaking of small flasks or sparging of fermentors. A preferred culture medium for *P. methanolica* is YEPD (2% D-glucose, 2% Bacto™ Peptone (Difco Laboratories, Detroit, Mich.), 1% Bacto™ yeast extract (Difco Laboratories), 0.004% adenine and 0.006% L-leucine).

Prokaryotic host cells, including strains of the bacteria *Escherichia coli*, Bacillus and other genera are also useful host cells within the present invention. Techniques for transforming those hosts and expressing foreign DNA sequences cloned therein are well known in the art (see, e.g., Sambrook et al., ibid.). When expressing a z219c polypeptide in bacteria such as *E. coli*, the polypeptide may be retained in the cytoplasm, typically as insoluble granules, or may be directed to the periplasmic space by a bacterial secretion sequence. In the former case, the cells are lysed, and the granules are recovered and denatured using, for example, guanidine isothiocyanate or urea. The denatured polypeptide can then be refolded and dimerized by diluting the denaturant, such as by dialysis against a solution of urea and a combination of reduced and oxidized glutathione, followed by dialysis against a buffered saline solution. In the latter case, the polypeptide can be recovered from the periplasmic space in a soluble and functional form by disrupting the cells (by, for example, sonication or osmotic shock) to release the contents of the periplasmic space and recovering the protein, thereby obviating the need for denaturation and refolding.

It is preferred to purify the polypeptides of the present invention to $\geq 80\%$ purity, more preferably to $\geq 90\%$ purity, even more preferably $\geq 95\%$ purity, and particularly preferred is a pharmaceutically pure state, that is greater than 99.9% pure with respect to contaminating macromolecules, particularly other proteins and nucleic acids, and free of infectious and pyrogenic agents. Preferably, a purified polypeptide is substantially free of other polypeptides, particularly other polypeptides of animal origin.

Expressed recombinant z219c polypeptides (or chimeric z219c polypeptides) can be purified using fractionation and/or conventional purification methods and media. Ammonium sulfate precipitation and acid or chaotrope extraction may be used for fractionation of samples. Exemplary purification steps may include hydroxyapatite, size exclusion, FPLC and reverse-phase high performance liquid chromatography. Suitable chromatographic media include derivatized dextrans, agarose, cellulose, polyacrylamide, specialty silicas, and the like. PEI, DEAE, QAE and Q derivatives are preferred. Exemplary chromatographic media include those media derivatized with phenyl, butyl, or octyl groups, such as Phenyl-Sepharose FF (Pharmacia), Toyopearl butyl 650 (Toso Haas, Montgomeryville, Pa.), Octyl-Sepharose (Pharmacia) and the like; or polyacrylic resins, such as Amberchrom CG 71 (Toso Haas) and the like. Suitable solids supports include glass beads, silica-based resins, cellulosic resins, agarose beads, cross-linked agarose beads, polystyrene beads, cross-linked polyacrylamide resins and the like that are insoluble under the conditions in which they are to be used. These supports may be modified with reactive groups that allow treatment of proteins by amino groups, carboxyl groups, sulfhydryl groups, hydroxyl groups and/or carbohydrate moieties. Examples of coupling chemistries include cyanogen bromide activation, N-hydroxysuccinimide activation, epoxide activation, sulfhydryl activation, hydrazide activation, and carboxyl and amino derivatives for carbodiimide coupling chemistries. These and other solid media are well known and widely used in the art, and are available from commercial suppliers. Methods for binding ligand or receptor polypeptides to support media are well known in the art. Selection of a particular method is a matter of routine design and is determined in part by the properties of the chosen support.

See, for example, *Affinity Chromatography: Principles & Methods,* Pharmacia LKB Biotechnology, Uppsala, Sweden, 1988.

The polypeptides of the present invention can be isolated by exploitation of their structural and biological properties. For example, immobilized metal ion adsorption (IMAC) chromatography can be used to purify histidine-rich proteins, including those comprising polyhistidine tags. Briefly, a gel is first charged with divalent metal ions to form a chelate (Sulkowski, *Trends in Biochem.* 3:1–7, 1985). Histidine-rich proteins will be adsorbed to this matrix with differing affinities, depending upon the metal ion used, and will be eluted by competitive elution, lowering the pH, or use of strong chelating agents. Other methods of purification include purification of glycosylated proteins by lectin affinity chromatography and ion exchange chromatography (*Methods in Enzymol.,* Vol. 182, "Guide to Protein Purification", M. Deutscher, (ed.), Acad. Press, San Diego, 1990, pp.529–39). Within additional embodiments of the invention, a fusion of the polypeptide of interest and an affinity tag (e.g., polyhistidine, maltose-binding protein, an immunoglobulin domain) may be constructed to facilitate purification.

Moreover, using methods described in the art, polypeptide fusions, or hybrid z219c proteins, are constructed using regions or domains of z219c in combination with those of other human 2–19 family proteins (e.g. human 2–19, D87120, and murine EF-7), or heterologous proteins (Sambrook et al., ibid., Altschul et al., ibid., Picard. D., *Cur. Opin. Biology,* 5:511–515, 1994, and references therein). These methods allow the determination of the biological importance of larger domains or regions in a polypeptide of interest. Such hybrids may alter reaction kinetics, binding, constrict or expand the substrate specificity, or alter tissue and cellular localization of a polypeptide, and can be applied to polypeptide of unknown structure.

Fusion polypeptides can be prepared by methods known to those skilled in the art by preparing each component of the fusion protein and chemically conjugating them. Alternatively, a polynucleotide encoding one or more components of the fusion protein in the proper reading frame can be generated using known techniques and expressed by the methods described herein. For example, part or all of a domain(s) conferring a biological function may be swapped between z219c of the present invention with the functionally equivalent domain(s) from another family member, such as human 2–19 protein or D87120. Such domains include, but are not limited to the secretory signal sequence, conserved motifs, and blocks 1, 2, and 3. Such fusion proteins would be expected to have a biological functional profile that is the same or similar to polypeptides of the present invention or other known 2–19 family proteins (e.g. human 2–19, D87120, and murine EF-7) or heterologous proteins, depending on the fusion constructed. Moreover, such fusion proteins may exhibit other properties as disclosed herein.

Standard molecular biological and cloning techniques can be used to swap and equivalent domains between the z219c polypeptide and those polypeptides to which they are fused. Generally, a DNA segment that encodes a domain of interest, e.g., a z219c domain described herein, is operably linked in frame to at least one other DNA segment encoding an additional polypeptide (for instance an analogous domain or region human 2–19 protein), and inserted into an appropriate expression vector, as described herein. Generally DNA constructs are made such that the several DNA segments that encode the corresponding regions of a polypeptide are operably linked in frame to make a single construct that encodes the entire fusion protein, or a functional portion thereof. For example, a DNA construct would encode from N-terminus to C-terminus a fusion protein comprising a signal polypeptide followed by a mature polypeptide; or a DNA construct would encode from N-terminus to C-terminus a fusion protein comprising a signal polypeptide followed by block 1, followed by block2, followed by block 3. Such fusion proteins can be expressed, isolated, and assayed for activity as described herein.

Protein refolding (and optionally reoxidation) procedures may be advantageously used. Z219c polypeptides or fragments thereof may also be prepared through chemical synthesis. Z219c polypeptides may be monomers or multimers; glycosylated or non-glycosylated; pegylated or non-pegylated; and may or may not include an initial methionine amino acid residue.

In view of the tissue distribution observed for this z219c polypeptide, agonists (including the natural ligand/substrate/cofactor/ etc.) and antagonists have enormous potential in both in vitro and in vivo applications. Compounds identified as z219c agonists are useful for growth, proliferation or differentiation of various cell types in vitro and treatment of diabetes, intestinal regeneration, gastric mucositis, mucosal regeneration, metabolic disorders, prostate disorders in vivo. For example, agonist compounds are useful as components of defined cell culture media, and may be used alone or in combination with other cytokines and hormones to replace serum that is commonly used in cell culture.

Within one embodiment, there is provided a method of identifying agonists of z219c polypeptide, comprising providing cells responsive to a z219c polypeptide, culturing a first portion of the cells in the presence of a test compound, culturing a second portion of the cells in the absence of a test compound, and detecting an increase in a cellular response of the first portion of the cells as compared to the second portion of the cells.

Within another embodiment, there is provided a method of identifying antagonists of z219c polypeptide, comprising providing cells responsive to a z219c polypeptide, culturing a first portion of the cells in the presence of z219c polypeptide, culturing a second portion of the cells in the presence of the z219c polypeptide and a test compound, and detecting a decrease in a cellular response of the second portion of the cells as compared to the first portion of the cells.

The activity of molecules of the present invention can be measured using a variety of assays that measure, for example, signal transduction upon binding a receptor, mucosal secretion, antibody binding, or ELISA. For example, z219c polypeptides can be labeled and tested for specific and saturating binding to specific cell lines or cells. After identification of positive cells to which z219c binds, activity can be tested for z219c-mediated activation of a signal transduction pathway using methods known in the art. For instance, vector constructs containing a reporter (e.g. SRE-luciferase or STAT-luciferase or the like) can be introduced into the positive cell lines; such cell lines, when exposed to conditioned media containing secreted z219c protein, will demonstrate z219c-mediated signal transduction activity through activation of the measurable reporter. Such assays are well known in the art. Specific assays include, but are not limited to bioassays measuring signal transduction.

In addition, z219c polypeptides of the present invention can be used to study pancreatic cell proliferation or differentiation. Such methods of the present invention generally comprise incubating α cells, β cells, δ cells, F cells and acinar cells in the presence and absence of z219c polypeptide, monoclonal antibody, agonist or antagonist thereof and observing changes in islet cell proliferation or differentiation.

A further aspect of the invention provides a method for studying insulin. Such methods of the present invention comprise incubating adipocytes in a culture medium comprising z219c polypeptides, monoclonal antibody, agonist or antagonist thereof ± insulin and observing changes in adipocyte protein secretion or differentiation.

The present invention also provides methods of studying mammalian cellular metabolism. Such methods of the present invention comprise incubating cells to be studies, for example, human vascular endothelial cells, ± z219c polypeptide, monoclonal antibody, agonist or antagonist thereof and observing changes in adipogenesis, gluconegenesis, glycogenolysis, lipogenesis, glucose uptake, or the like.

A high level of expression of z219c polypeptide was observed by Northern blot in the trachea and by dot blot in the salivary gland and trachea. Consequently, another aspect of the present invention involves the detection of z219c polypeptides in the serum or tissue biopsy of a patient undergoing evaluation for salivary gland function or dysfunction. Such z219c polypeptides can be detected using immunoassay techniques and antibodies capable of recognizing z219c polypeptide epitopes.

More specifically, the present invention contemplates methods for detecting z219c polypeptide comprising:

exposing a solution possibly containing z219c polypeptide to an antibody attached to a solid support, wherein said antibody binds to a first epitope of a z219c polypeptide;

washing said immobilized antibody-polypeptide to remove unbound contaminants;

exposing the immobilized antibody-polypeptide to a second antibody directed to a second epitope of a z219c polypeptide, wherein the second antibody is associated with a detectable label; and detecting the detectable label. Changes in serum or biopsy z219c polypeptide concentration (relative to normal serum or tissue concentration) may be indicative of dysfunction of the salivary gland.

Salivary gland dysfunction includes digestive dysfunction, wound healing dysfunction, inadequate saliva production or composition, mucosal integrity breakdown, and failure of or diminished anti-microbial function. Detection of z219c polypeptide at relatively high levels in the trachea may indicate that such polypeptides may serve as a marker of lung dysfunction. Moreover, z219c expression is detected in lung. Examples of conditions associated with salivary gland or lung dysfunction include salivary gland carcinoma, sarcoidosis, pneumocystic carinii (particularly as associated with AIDS patients), emphysema, chronic bronchitis, cystic fibrosis, ARDS, SIDS or the like. In addition, z219c polypeptides are expressed in the prostate at a level similar to trachea, as well as in the salivary gland. The prostate gland is androgen regulated and shares other properties with salivary glands. Consequently, dysfunction thereof, such as prostate adenocarcinoma or the like, may also be detected using z219c polypeptides or z219c antibodies.

Also, the salivary glands synthesize and secrete a number of proteins having diverse biological functions. Such proteins facilitate lubrication of the oral cavity (e.g., mucins and proline-rich proteins), remineralization (e.g., statherin and ionic proline-rich proteins) and digestion (e.g., amylase, lipase and proteases) and provide anti-microbial (e.g., proline-rich proteins, lysozyme, histatins and lactoperoxidase) and mucosal integrity maintenance (e.g., mucins) capabilities. In addition, saliva is a rich source of growth factors synthesized by the salivary glands. For example, saliva is known to contain epidermal growth factor (EGF), nerve growth factor (NGF), transforming growth factor-alpha (TGF-α), transforming growth factor-beta (TGF-β), insulin, insulin-like growth factors I and II (IGF-I and IGF-II) and fibroblast growth factor (FGF). See, for example, Zelles et al., *J. Dental. Res.* 74(12): 1826–32, 1995. Synthesis of growth factors by the salivary gland is believed to be androgen-dependent and to be necessary for the health of the oral cavity and gastrointestinal tract.

Thus, z219c polypeptides, agonists or antagonists thereof may be therapeutically useful for aiding digestion. To verify the presence of this capability in z219c polypeptides, agonists or antagonists of the present invention, such z219c polypeptides, agonists or antagonists are evaluated with respect to their ability to break down starch according to procedures known in the art. If desired, z219c polypeptide performance in this regard can be compared to digestive enzymes, such as amylase, lipase, proteases and the like. In addition, z219c polypeptides or agonists or antagonists thereof may be evaluated in combination with one or more digestive enzymes to identify synergistic effects.

Also, z219c polypeptides, agonists or antagonists thereof may be therapeutically useful for promoting wound healing. To verify the presence of this capability in z219c polypeptides, agonists or antagonists of the present invention, such z219c polypeptides, agonists or antagonists are evaluated with respect to their ability to facilitate wound healing according to procedures known in the art. If desired, z219c polypeptide performance in this regard can be compared to growth factors, such as EGF, NGF, TGF-α, TGF-β, insulin, IGF-I, IGF-II, fibroblast growth factor (FGF) and the like. In addition, z219c polypeptides or agonists or antagonists thereof may be evaluated in combination with one or more growth factors to identify synergistic effects.

In addition, z219c polypeptides, agonists or antagonists thereof may be therapeutically useful for anti-microbial applications. To verify the presence of this capability in z219c polypeptides, agonists or antagonists of the present invention, such z219c polypeptides, agonists or antagonists are evaluated with respect to their antimicrobial properties according to procedures known in the art. See, for example, Barsum et al., *Eur. Respir. J.* 8(5): 709–14, 1995; Sandovsky-Losica et al., *J. Med. Vet. Mycol (England)* 28(4): 279–87, 1990; Mehentee et al., *J. Gen. Microbiol (England)* 135 (Pt. 8): 2181–8, 1989; Segal and Savage, *Journal of Medical and Veterinary Mycology* 24: 477–479, 1986 and the like. If desired z219c polypeptide performance in this regard can be compared to proteins known to be functional in this regard, such as proline-rich proteins, lysozyme, histatins, lactoperoxidase or the like. In addition, z219c polypeptides or agonists or antagonists thereof may be evaluated in combination with one or more antimicrobial agents to identify synergistic effects.

The activity of molecules of the present invention can be measured using a variety of assays that measure stimulation of gastrointestinal cell contractility, modulation of nutrient uptake and/or secretion of digestive enzymes. Of particular interest are changes in contractility of smooth muscle cells. For example, the contractile response of segments of mammalian duodenum or other gastrointestinal smooth muscles tissue (Depoortere et al., *J. Gastrointestinal Motility* 1:150–159, 1989). An exemplary in vivo assay uses an ultrasonic micrometer to measure the dimensional changes radially between commissures and longitudinally to the plane of the valve base (Hansen et al., *Society of Thoracic Surgeons* 60:S384–390, 1995).

Anti-microbial protective agents may be directly acting or indirectly acting. Such agents operating via membrane association or pore forming mechanisms of action directly attach to the offending microbe. Anti-microbial agents can also act via an enzymatic mechanism, breaking down microbial protective substances or the cell wall/membrane thereof. Anti-microbial agents, capable of inhibiting microorganism proliferation or action or of disrupting microorganism integrity by either mechanism set forth above, are useful in methods for preventing contamination in cell culture by microbes susceptible to that anti-microbial activity. Such techniques involve culturing cells in the presence of an effective amount of said z219c polypeptide or an agonist or antagonist thereof.

Also, z219c polypeptides or agonists thereof may be used as cell culture reagents in in vitro studies of exogenous microorganism infection, such as bacterial, viral or fungal infection. Such moieties may also be used in in vivo animal models of infection. Also, the microorganism-adherence properties of z219c polypeptides or agonists thereof can be studied under a variety of conditions in binding assays and the like.

Moreover, z219c polypeptides, agonists or antagonists thereof may be therapeutically useful for mucosal integrity maintenance. Tissue expression of z219c is moderate to high in tissues involved in mucosal secretion, such as small intestine, trachea and salivary gland. To verify this presence of this capability in z219c polypeptides, agonists or antagonists of the present invention, such z219c polypeptides, agonists or antagonists are evaluated with respect to their mucosal integrity maintenance according to procedures known in the art. See, for example, Zahm et al., *Eur. Respir. J.* 8: 381–6, 1995, which describes methods for measuring viscoelastic properties and surface properties of mucous as well as for evaluating mucous transport by cough and by ciliary activity. If desired, z219c polypeptide performance in this regard can be compared to mucins or the like. In addition, z219c polypeptides or agonists or antagonists thereof may be evaluated in combination with mucins to identify synergistic effects.

Proteins of the present invention are useful for example, in treating intestinal, prostate, and pancreatic disorders, and can be measured in vitro using cultured cells or in vivo by administering molecules of the present invention to the appropriate animal model. For instance, host cells expressing a z219c soluble receptor polypeptide can be embedded in an alginate environment and injected (implanted) into recipient animals. Alginate-poly-L-lysine microencapsulation, permselective membrane encapsulation and diffusion chambers are a means to entrap transfected mammalian cells or primary mammalian cells. These types of non-immunogenic "encapsulations" permit the diffusion of proteins and other macromolecules secreted or released by the captured cells to the recipient animal. Most importantly, the capsules mask and shield the foreign, embedded cells from the recipient animal's immune response. Such encapsulations can extend the life of the injected cells from a few hours or days (naked cells) to several weeks (embedded cells). Alginate threads provide a simple and quick means for generating embedded cells.

The materials needed to generate the alginate threads are known in the art. In an exemplary procedure, 3% alginate is prepared in sterile $H_2O$, and sterile filtered. Just prior to preparation of alginate threads, the alginate solution is again filtered. An approximately 50% cell suspension (containing about $5 \times 10^5$ to about $5 \times 10^7$ cells/ml) is mixed with the 3% alginate solution. One ml of the alginate/cell suspension is extruded into a 100 mM sterile filtered $CaCl_2$ solution over a time period of ~15 min, forming a "thread". The extruded thread is then transferred into a solution of 50 mM $CaCl_2$, and then into a solution of 25 mM $CaCl_2$. The thread is then rinsed with deionized water before coating the thread by incubating in a 0.01% solution with poly-L-lysine. Finally, the thread is rinsed with Lactated Ringer's Solution and drawn from solution into a syringe barrel (without needle). A large bore needle is then attached to the syringe, and the thread is intraperitoneally injected into a recipient in a minimal volume of the Lactated Ringer's Solution.

An in vivo approach for assaying proteins of the present invention involves viral delivery systems. Exemplary viruses for this purpose include adenovirus, herpesvirus, retroviruses, vaccinia virus, and adeno-associated virus (AAV). Adenovirus, a double-stranded DNA virus, is currently the best studied gene transfer vector for delivery of heterologous nucleic acid (for review, see T. C. Becker et al., *Meth. Cell Biol.* 43:161–89, 1994; and J. T. Douglas and D. T. Curiel, *Science & Medicine* 4:44–53, 1997). The adenovirus system offers several advantages: (i) adenovirus can accommodate relatively large DNA inserts; (ii) can be grown to high-titer; (iii) infect a broad range of mammalian cell types; and (iv) can be used with many different promoters including ubiquitous, tissue specific, and regulatable promoters. Also, because adenoviruses are stable in the bloodstream, they can be administered by intravenous injection.

Using adenovirus vectors where portions of the adenovirus genome are deleted, inserts are incorporated into the viral DNA by direct ligation or by homologous recombination with a co-transfected plasmid. In an exemplary system, the essential E1 gene has been deleted from the viral vector, and the virus will not replicate unless the E1 gene is provided by the host cell (the human 293 cell line is exemplary). When intravenously administered to intact animals, adenovirus primarily targets the liver. If the adenoviral delivery system has an E1 gene deletion, the virus cannot replicate in the host cells. However, the host's tissue (e.g., liver) will express and process (and, if a secretory signal sequence is present, secrete) the heterologous protein. Secreted proteins will enter the circulation in the highly vascularized liver, and effects on the infected animal can be determined.

Moreover, adenoviral vectors containing various deletions of viral genes can be used in an attempt to reduce or eliminate immune responses to the vector. Such adenoviruses are E1 deleted, and in addition contain deletions of E2A or E4 (Lusky, M. et al., *J. Virol.* 72:2022–2032, 1998; Raper, S. E. et al., *Human Gene Therapy* 9:671–679, 1998). In addition, deletion of E2b is reported to reduce immune responses (Amalfitano, A. et al., *J. Virol.* 72:926–933, 1998). Moreover, by deleting the entire adenovirus genome, very large inserts of heterologous DNA can be accommodated. Generation of so called "gutless" adenoviruses where all viral genes are deleted are particularly advantageous for insertion of large inserts of heterologous DNA. For review, see Yeh, P. and Perricaudet, M., *FASEB J.* 11:615–623, 1997.

The adenovirus system can also be used for protein production in vitro. By culturing adenovirus-infected non-293 cells under conditions where the cells are not rapidly dividing, the cells can produce proteins for extended periods of time. For instance, BHK cells are grown to confluence in cell factories, then exposed to the adenoviral vector encoding the secreted protein of interest. The cells are then grown under serum-free conditions, which allows infected cells to survive for several weeks without significant cell division. Alternatively, adenovirus vector infected 293 cells can be grown as adherent cells or in suspension culture at relatively high cell density to produce significant amounts of protein (See Garnier et al., *Cytotechnol.* 15:145–55, 1994). With either protocol, an expressed, secreted heterologous protein can be repeatedly isolated from the cell culture supernatant, lysate, or membrane fractions depending on the disposition of the expressed protein in the cell. Within the infected 293 cell production protocol, non-secreted proteins may also be effectively obtained.

Compounds identified as z219c agonists are useful in vitro and in vivo. For example, z219c and agonist compounds are useful as components of defined cell culture media, and may be used alone or in combination with other cytokines and hormones to replace serum that is commonly used in cell culture. Thus, z219c polypeptides and z219c agonist polypeptides are useful as a research reagent, such as for the expansion of cultured cells. As such, z219c polypeptides are added to tissue culture media for these cell types.

As a ligand, the activity of z219c polypeptide can be measured by a silicon-based biosensor microphysiometer which measures the extracellular acidification rate or proton excretion associated with receptor binding and subsequent physiologic cellular responses. An exemplary device is the Cytosensor™ Microphysiometer manufactured by Molecular Devices, Sunnyvale, Calif. A variety of cellular responses, such as cell proliferation, ion transport, energy production, inflammatory response, regulatory and receptor activation, and the like, can be measured by this method. See, for example, McConnell, H. M. et al., *Science* 257:1906–1912, 1992; Pitchford, S. et al., *Meth. Enzymol.* 228:84–108, 1997; Arimilli, S. et al., *J. Immunol. Meth.* 212:49–59, 1998; Van Liefde, I. et al., *Eur. J. Pharmacol.* 346:87–95, 1998. The microphysiometer can be used for assaying adherent or non-adherent eukaryotic or prokaryotic cells. By measuring extracellular acidification changes in cell media over time, the microphysiometer directly measures cellular responses to various stimuli, including z219c polypeptide, its agonists, or antagonists. Preferably, the microphysiometer is used to measure responses of a z219c-responsive eukaryotic cell, compared to a control eukaryotic cell that does not respond to z219c polypeptide, z219c-responsive eukaryotic cells comprise cells into which a receptor for z219c has been transfected creating a cell that is responsive to z219c; or cells naturally responsive to z219c such as cells derived from, for example, pancreas, intestinal, prostate or tracheal tissue. Differences, measured by a change, for example, an increase or diminution in extracellular acidification, in the response of cells exposed to z219c polypeptide, relative to a control not exposed to z219c, are a direct measurement of z219c-modulated cellular responses. Moreover, such z219c-modulated responses can be assayed under a variety of stimuli. Using the microphysiometer, there is provided a method of identifying agonists of z219c polypeptide, comprising providing cells responsive to a z219c polypeptide, culturing a first portion of the cells in the absence of a test compound, culturing a second portion of the cells in the presence of a test compound, and detecting a change, for example, an increase or diminution, in a cellular response of the second portion of the cells as compared to the first portion of the cells. The change in cellular response is shown as a measurable change extracellular acidification rate. Moreover, culturing a third portion of the cells in the presence of z219c polypeptide and the absence of a test compound can be used as a positive control for the z219c-responsive cells, and as a control to compare the agonist activity of a test compound with that of the z219c polypeptide. Moreover, using the microphysiometer, there is provided a method of identifying antagonists of z219c polypeptide, comprising providing cells responsive to a z219c polypeptide, culturing a first portion of the cells in the presence of z219c and the absence of a test compound, culturing a second portion of the cells in the presence of z219c and the presence of a test compound, and detecting a change, for example, an increase or a diminution in a cellular response of the second portion of the cells as compared to the first portion of the cells. The change in cellular response is shown as a measurable change extracellular acidification rate. Antagonists and agonists, for z219c polypeptide, can be rapidly identified using this method.

Moreover, z219c can be used to identify cells, tissues, or cell lines which respond to a z219c-stimulated pathway. The microphysiometer, described above, can be used to rapidly identify ligand-responsive cells, such as cells responsive to z219c of the present invention. Cells can be cultured in the presence or absence of z219c polypeptide. Those cells which elicit a measurable change in extracellular acidification in the presence of z219c are responsive to z219c. Such cells, can be used to identify antagonists and agonists of z219c polypeptide as described above.

z219c can also be used to identify inhibitors (antagonists) of its activity. Test compounds are added to the assays disclosed herein to identify compounds that inhibit the activity of z219c. In addition to those assays disclosed herein, samples can be tested for inhibition of z219c activity within a variety of assays designed to measure receptor binding or the stimulation/inhibition of z219c-dependent cellular responses. For example, z219c-responsive cell lines can be transfected with a reporter gene construct that is responsive to a z219c-stimulated cellular pathway. Reporter gene constructs of this type are known in the art, and will generally comprise a z219c-DNA response element operably linked to a gene encoding an assayable protein, such as luciferase. DNA response elements can include, but are not limited to, cyclic AMP response elements (CRE), hormone response elements (HRE) insulin response element (IRE) (Nasrin et al., *Proc. Natl. Acad. Sci. USA* 87:5273–7, 1990) and serum response elements (SRE) (Shaw et al. *Cell* 56:563–72, 1989). Cyclic AMP response elements are reviewed in Roestler et al., *J. Biol. Chem.* 263 (19):9063–6; 1988 and Habener, *Molec. Endocrinol.* 4 (8):1087–94; 1990. Hormone response elements are reviewed in Beato, *Cell* 56:335–44; 1989. Candidate compounds, solutions, mixtures or extracts are tested for the ability to inhibit the activity of z219c on the target cells as evidenced by a decrease in z219c stimulation of reporter gene expression. Assays of this type will detect compounds that directly block z219c binding to cell-surface receptors, as well as compounds that block processes in the cellular pathway subsequent to receptor-ligand binding. In the alternative, compounds or other samples can be tested for direct blocking of z219c binding to receptor using z219c tagged with a detectable label (e.g., $^{125}$I, biotin, horseradish peroxidase, FITC, and the like). Within assays of this type, the ability of a test sample to inhibit the binding of labeled z219c to the receptor is indicative of inhibitory activity, which can be confirmed through secondary assays. Receptors used within binding assays may be cellular receptors or isolated, immobilized receptors.

A z219c polypeptide can be expressed as a fusion with an immunoglobulin heavy chain constant region, typically an $F_C$ fragment, which contains two constant region domains and lacks the variable region. Methods for preparing such fusions are disclosed in U.S. Pat. Nos. 5,155,027 and 5,567,584. Such fusions are typically secreted as multimeric molecules wherein the Fc portions are disulfide bonded to each other and two non-Ig polypeptides are arrayed in closed proximity to each other. Fusions of this type can be used to affinity purify z219c receptor, as an in vitro assay tool, or as a z219c antagonist. For use in assays, the chimeras are bound to a support via the $F_C$ region and used in an ELISA format.

Z219c polypeptides can also be used to prepare antibodies that specifically bind to z219c epitopes, peptides or polypeptides. The z219c polypeptide or a fragment thereof serves as an antigen (immunogen) to inoculate an animal and elicit an immune response. One of skill in the art would recognize that antigens or immunogenic epitopes can consist of stretches of amino acids within a longer polypeptide from about 10 amino acids or longer, and up to about the entire length of the polypeptide or longer depending on the polypeptide. Thus, suitable antigens include a polypeptide consisting of 9 to 210 amino acids, wherein the polypeptide is at least 90% identical to a contiguous sequence of amino acids in SEQ ID NO:2 from amino acid number 23 (Phe), to amino acid number 223 (Phe). Suitable antigens also include the mature z219c polypeptide, z219c secretory signal sequence, blocks 1, 2 and 3, the N-terminus of the mature polypeptide (SEQ ID NO:2 from amino acid number 22 (Phe) to amino acid number 88 (Ile) of SEQ ID NO:2), as disclosed herein and amino acid sequences within these regions. Peptides used for immunizing animals are generally from about 9 to about 80 amino acids in length; however longer regions or full-length z219c proteins can also be used as immunogens. Preferred peptides to use as antigens are hydrophilic peptides such as those predicted by one of skill in the art from a hydrophobicity plot, determined for example, from a Hopp/Woods hydrophilicity profile based on a sliding six-residue window, with buried G, S, and T residues and exposed H, Y, and W residues ignored. Antibodies generated from this immune response can be isolated and purified as described herein. Methods for preparing and isolating polyclonal and monoclonal antibodies are well known in the art. See, for example, *Current Protocols in Immunology*, Cooligan, et al. (eds.), National Institutes of Health, John Wiley and Sons, Inc., 1995; Sambrook et al., *Molecular Cloning: A Laboratory Manual, Second Edition*, Cold Spring Harbor, NY, 1989; and Hurrell, J. G. R., Ed., *Monoclonal Hybridoma Antibodies: Technique and Applications*, CRC Press, Inc., Boca Raton, Fla., 1982.

As would be evident to one of ordinary skill in the art, antibodies can be generated from inoculating a variety of warm-blooded animals such as horses, cows, goats, sheep, dogs, chickens, rabbits, mice, and rats with a z219c polypeptide or a fragment thereof. The immunogenicity of a z219c polypeptide may be increased through the use of an adjuvant, such as alum (aluminum hydroxide) or Freund's complete or incomplete adjuvant. Polypeptides useful for immunization also include fusion polypeptides, such as fusions of z219c polypeptide or a portion thereof with an immunoglobulin polypeptide or with maltose binding protein. The polypeptide immunogen may be a full-length molecule or a portion thereof. If the polypeptide portion is "hapten-like", such portion may be advantageously joined or linked to a macromolecular carrier (such as keyhole limpet hemocyanin (KLH), bovine serum albumin (BSA) or tetanus toxoid) for immunization.

As used herein, the term "antibodies" includes polyclonal antibodies, affinity-purified polyclonal antibodies, monoclonal antibodies, and antigen-binding fragments, such as $F(ab')_2$ and Fab proteolytic fragments. Genetically engineered intact antibodies or fragments, such as chimeric antibodies, Fv fragments, single chain antibodies and the like, as well as synthetic antigen-binding peptides and polypeptides, are also included. Non-human antibodies may be humanized by grafting non-human CDRs onto human framework and constant regions, or by incorporating the entire non-human variable domains (optionally "cloaking" them with a human-like surface by replacement of exposed residues, wherein the result is a "veneered" antibody). In some instances, humanized antibodies may retain non-human residues within the human variable region framework domains to enhance proper binding characteristics. Through humanizing antibodies, biological half-life may be increased, and the potential for adverse immune reactions upon administration to humans is reduced.

Alternative techniques for generating or selecting antibodies useful herein include in vitro exposure of lymphocytes to z219c polypeptide or peptide, and selection of antibody display libraries in phage or similar vectors (for instance, through use of immobilized or labeled z219c polypeptide). Genes encoding polypeptides having potential z219c polypeptide binding domains can be obtained by screening random peptide libraries displayed on phage (phage display) or on bacteria, such as *E. coli*. Nucleotide sequences encoding the polypeptides can be obtained in a number of ways, such as through random mutagenesis and random polynucleotide synthesis. These random peptide display libraries can be used to screen for peptides which interact with a known target which can be a protein or polypeptide, such as a ligand or receptor, a biological or synthetic macromolecule, or organic or inorganic substances. Techniques for creating and screening such random peptide display libraries are known in the art (Ladner et al., U.S. Pat. No. 5,223,409; Ladner et al., U.S. Pat. No. 4,946,778; Ladner et al., U.S. Pat. No. 5,403,484 and Ladner et al., U.S. Pat. No. 5,571,698) and random peptide display libraries and kits for screening such libraries are available commercially, for instance from Clontech (Palo Alto, Calif.), Invitrogen Inc. (San Diego, Calif.), New England Biolabs, Inc. (Beverly, Mass.) and Pharmacia LKB Biotechnology Inc. (Piscataway, N.J.). Random peptide display libraries can be screened using the z219c sequences disclosed herein to identify polypeptides which bind to z219c. These "binding polypeptides" which interact with z219c polypeptides can be used for tagging cells; for isolating homolog polypeptides by affinity purification; they can be directly or indirectly conjugated to drugs, toxins, radionuclides and the like. These binding polypeptides can also be used in analytical methods such as for screening expression libraries and neutralizing z219c activity. The binding polypeptides can also be used for diagnostic assays for determining circulating levels of z219c polypeptides; for detecting or quantitating soluble polypeptides as marker of underlying pathology or disease. These binding polypeptides can also act as z219c "antagonists" to block z219c binding, for example, to a receptor, and to block signal transduction in vitro and in vivo. These anti-z219c binding polypeptides would be useful, for example, as antagonists for inhibiting z219c ligand from interacting with its receptor.

Antibodies are determined to be specifically binding if: 1) they exhibit a threshold level of binding activity, and/or 2) they do not significantly cross-react with known related polypeptide molecules. First, antibodies herein specifically bind if they bind to a z219c polypeptide, peptide or epitope with an affinity at least 10-fold greater than the binding affinity to control (non-z219c) polypeptide. It is preferred that the antibodies exhibit a binding affinity ($K_a$) of $10^6$ $M^{-1}$ or greater, preferably $10^7$ $M^{-1}$ or greater, more preferably $10^8$ $M^{-1}$ or greater, and most preferably $10^9$ $M^{-1}$ or greater. The binding affinity of an antibody can be readily determined by one of ordinary skill in the art, for example, by Scatchard analysis (Scatchard, G., *Ann. NY Acad. Sci.* 51: 660–672, 1949).

Second, antibodies are determined to specifically bind if they do not significantly cross-react with known related polypeptides. Antibodies do not significantly cross-react with related polypeptide molecules, for example, if they detect z219c but not known related polypeptides using a standard Western blot analysis (Ausubel et al., ibid.). Examples of known related polypeptides are orthologs, polypeptides from the same species that are members of a protein family such as other known 2–19 family members, mutant z219c polypeptides, and non-human z219c. Moreover, antibodies may be "screened against" known related polypeptides to isolate a population that specifically binds to the inventive polypeptides. For example, antibodies raised to z219c are adsorbed to related polypeptides adhered to insoluble matrix; antibodies specific to z219c will flow through the matrix under the proper buffer conditions. Such screening allows isolation of polyclonal and monoclonal antibodies non-crossreactive to closely related polypeptides (*Antibodies: A Laboratory Manual,* Harlow and Lane (eds.), Cold Spring Harbor Laboratory Press, 1988; *Current Protocols in Immunology,* Cooligan, et al. (eds.), National Institutes of Health, John Wiley and Sons, Inc., 1995). Screening and isolation of specific antibodies is well known in the art. See, *Fundamental Immunology,* Paul (eds.), Raven Press, 1993; Getzoff et al., *Adv. in Immunol.* 43: 1–98, 1988; *Monoclonal Antibodies: Principles and Practice,* Goding, J. W. (eds.), *Academic Press Ltd.,* 1996; Benjamin et al., *Ann. Rev. Immunol.* 2: 67–101, 1984.

A variety of assays known to those skilled in the art can be utilized to detect antibodies which specifically bind to z219c polypeptides or peptides. Exemplary assays are described in detail in *Antibodies: A Laboratory Manual,* Harlow and Lane (Eds.), Cold Spring Harbor Laboratory Press, 1988. Representative examples of such assays include: concurrent immunoelectrophoresis, radioimmunoassay, radioimmuno-precipitation, enzyme-linked immunosorbent assay (ELISA), dot blot or Western blot assay, inhibition or competition assay, and sandwich assay. In addition, antibodies can be screened for binding to wild-type versus mutant z219c polypeptide.

Antibodies to z219c may be used for tagging cells that express z219c; for isolating z219c by affinity purification; for diagnostic assays for determining circulating levels of z219c polypeptides; for detecting or quantitating soluble z219c as marker of underlying pathology or disease; in analytical methods employing FACS; in analytical methods employing in situ hybridization and histology; for screening expression libraries; for generating anti-idiotypic antibodies; and as neutralizing antibodies or as antagonists to block z219c activity in vitro and in vivo. Suitable direct tags or labels include radionuclides, enzymes, substrates, cofactors, inhibitors, fluorescent markers, chemiluminescent markers, magnetic particles and the like; indirect tags or labels may feature use of biotin-avidin or other complement/anti-complement pairs as intermediates. Antibodies herein may also be directly or indirectly conjugated to drugs, toxins, radionuclides and the like, and these conjugates used for in vivo diagnostic or therapeutic applications. Moreover, antibodies to z219c polypeptide or fragments thereof may be used in vitro to detect denatured z219c polypeptide or fragments thereof in assays, for example, Western Blots or other assays known in the art.

Antibodies or polypeptides herein can also be directly or indirectly conjugated to drugs, toxins, radionuclides and the like, and these conjugates used for in vivo diagnostic or therapeutic applications. For instance, polypeptides or antibodies of the present invention can be used to identify or treat tissues or organs that express a corresponding anti-complementary molecule (receptor or antigen, respectively, for instance). More specifically, z219c polypeptides or anti-z219c antibodies, or bioactive fragments or portions thereof, can be coupled to detectable or cytotoxic molecules and delivered to a mammal having cells, tissues or organs that express the anti-complementary molecule.

Suitable detectable molecules may be directly or indirectly attached to the polypeptide or antibody, and include radionuclides, enzymes, substrates, cofactors, inhibitors, fluorescent markers, chemiluminescent markers, magnetic particles and the like. Suitable cytotoxic molecules may be directly or indirectly attached to the polypeptide or antibody, and include bacterial or plant toxins (for instance, diphtheria toxin, Pseudomonas exotoxin, ricin, abrin and the like), as well as therapeutic radionuclides, such as iodine-131, rhenium-188 or yttrium-90 (either directly attached to the polypeptide or antibody, or indirectly attached through means of a chelating moiety, for instance). Polypeptides or antibodies may also be conjugated to cytotoxic drugs, such as adriamycin. For indirect attachment of a detectable or cytotoxic molecule, the detectable or cytotoxic molecule can be conjugated with a member of a complementary/anticomplementary pair, where the other member is bound to the polypeptide or antibody portion. For these purposes, biotin/streptavidin is an exemplary complementary/anticomplementary pair.

In another embodiment, polypeptide-toxin fusion proteins or antibody-toxin fusion proteins can be used for targeted cell or tissue inhibition or ablation (for instance, to treat cancer cells or tissues). Alternatively, if the polypeptide has multiple functional domains (i.e., an activation domain or a ligand binding domain, plus a targeting domain), a fusion protein including only the targeting domain may be suitable for directing a detectable molecule, a cytotoxic molecule or a complementary molecule to a cell or tissue type of interest. In instances where the domain only fusion protein includes a complementary molecule, the anti-complementary molecule can be conjugated to a detectable or cytotoxic molecule. Such domain-complementary molecule fusion proteins thus represent a generic targeting vehicle for cell/tissue-specific delivery of generic anti-complementary-detectable/cytotoxic molecule conjugates.

In another embodiment, z219c-cytokine fusion proteins or antibody-cytokine fusion proteins can be used for enhancing in vivo killing of target tissues (for example, blood and bone marrow cancers), if the z219c polypeptide or anti-z219c antibody targets the hyperproliferative blood or bone marrow cell (See, generally, Hornick et al., *Blood* 89:4437–47, 1997). They described fusion proteins enable targeting of a cytokine to a desired site of action, thereby providing an elevated local concentration of cytokine. Suitable z219c polypeptides or anti-z219c antibodies target an undesirable cell or tissue (i.e., a tumor or a leukemia), and the fused cytokine mediated improved target cell lysis by effector cells. Suitable cytokines for this purpose include interleukin 2 and granulocyte-macrophage colony-stimulating factor (GM-CSF), for instance.

In yet another embodiment, the z219c polypeptide or anti-z219c antibody can target vascular cells or tissues. Such polypeptide or antibody can be conjugated with a radionuclide, and particularly with a beta-emitting radionuclide, to reduce restenosis. Such therapeutic approach poses less danger to clinicians who administer the radioactive therapy. For instance, iridium-192 impregnated ribbons placed into stented vessels of patients until the required radiation dose was delivered showed decreased tissue growth in the vessel and greater luminal diameter than the control group, which received placebo ribbons. Further, revascularisation and stent thrombosis were significantly lower in the treatment group. Similar results are predicted with targeting of a bioactive conjugate containing a radionuclide, as described herein.

The bioactive polypeptide or antibody conjugates described herein can be delivered intravenously, intraarterially or intraductally, or may be introduced locally at the intended site of action.

Molecules of the present invention can be used to identify and isolate receptors for z219c. For example, proteins and peptides of the present invention can be immobilized on a column and membrane preparations run over the column (*Immobilized Affinity Ligand Techniques,* Hermanson et al., eds., Academic Press, San Diego, Calif., 1992, pp. 195–202). Proteins and peptides can also be radiolabeled (*Methods in Enzymol.,* vol. 182, "Guide to Protein Purification", M. Deutscher, ed., Acad. Press, San Diego, 1990, 721–737) or photoaffinity labeled (Brunner et al., *Ann. Rev. Biochem.* 62:483–514, 1993 and Fedan et al., *Biochem. Pharmacol.* 33:1167–1180, 1984) and specific cell-surface proteins can be identified.

The polypeptides, nucleic acid and/or antibodies of the present invention can be used in treatment and evaluation of disorders associated with type I and type II diabetes, gestational diabetes, pancreatic cancer, nutrient and metabolic disorders, pancreatic and intestinal hormonal release, intestinal mucosal secretion, intestinal regeneration from acute injury, peptic ulcers, Crohn's disease, inflammatory bowel disease, defense of the GI tract against microbial attack, throat and tracheal cancer, stomach cancer, colon cancer, intestinal cancer, diverticulitis, other epithelial disorders, and prostate obstruction and cancer. The molecules of the present invention can be used to modulate other proteins to which they interact, or to treat or prevent development of pathological conditions in such diverse tissues as trachea, small intestine, pancreas, and colon. In particular, certain diseases such as diabetes, cancer, peptic ulcers, Crohn's disease, inflammatory bowel disease, certain genetic syndromes and other human diseases may be amenable to such diagnosis, treatment or prevention.

Polynucleotides encoding z219c polypeptides are useful within gene therapy applications where it is desired to increase or inhibit z219c activity. If a mammal has a mutated or absent z219c gene, the z219c gene can be introduced into the cells of the mammal. In one embodiment, a gene encoding a z219c polypeptide is introduced in vivo in a viral vector. Such vectors include an attenuated or defective DNA virus, such as, but not limited to, herpes simplex virus (HSV), papillomavirus, Epstein Barr virus (EBV), adenovirus, adeno-associated virus (AAV), and the like. Defective viruses, which entirely or almost entirely lack viral genes, are preferred. A defective virus is not infective after introduction into a cell. Use of defective viral vectors allows for administration to cells in a specific, localized area, without concern that the vector can infect other cells. Examples of particular vectors include, but are not limited to, a defective herpes simplex virus 1 (HSV1) vector (Kaplitt et al., *Molec. Cell. Neurosci.* 2:320–30, 1991); an attenuated adenovirus vector, such as the vector described by Stratford-Perricaudet et al., *J. Clin. Invest.* 90:626–30, 1992; and a defective adeno-associated virus vector (Samulski et al., *J. Virol.* 61:3096–101, 1987; Samulski et al., *J. Virol.* 63:3822–8, 1989).

In another embodiment, a z219c gene can be introduced in a retroviral vector, e.g., as described in Anderson et al., U.S. Pat. No. 5,399,346; Mann et al. *Cell* 33:153, 1983; Temin et al., U.S. Pat. No. 4,650,764; Temin et al., U.S. Pat. No. 4,980,289; Markowitz et al., *J. Virol.* 62:1120, 1988; Temin et al., U.S. Pat. No. 5,124,263; International Patent Publication No. WO 95/07358, published Mar. 16, 1995 by Dougherty et al.; and Kuo et al., *Blood* 82:845, 1993. Alternatively, the vector can be introduced by lipofection in vivo using liposomes. Synthetic cationic lipids can be used to prepare liposomes for in vivo transfection of a gene encoding a marker (Felgner et al., *Proc. Natl. Acad. Sci. USA* 84:7413–7, 1987; Mackey et al., *Proc. Natl. Acad. Sci. USA* 85:8027–31, 1988). The use of lipofection to introduce exogenous genes into specific organs in vivo has certain practical advantages. Molecular targeting of liposomes to specific cells represents one area of benefit. More particularly, directing transfection to particular cells represents one area of benefit. For instance, directing transfection to particular cell types would be particularly advantageous in a tissue with cellular heterogeneity, such as the pancreas, liver, kidney, and brain. Lipids may be chemically coupled to other molecules for the purpose of targeting. Targeted peptides (e.g., hormones or neurotransmitters), proteins such as antibodies, or non-peptide molecules can be coupled to liposomes chemically.

It is possible to remove the target cells from the body; to introduce the vector as a naked DNA plasmid; and then to re-implant the transformed cells into the body. Naked DNA vectors for gene therapy can be introduced into the desired host cells by methods known in the art, e.g., transfection, electroporation, microinjection, transduction, cell fusion, DEAE dextran, calcium phosphate precipitation, use of a gene gun or use of a DNA vector transporter. See, e.g., Wu et al., *J. Biol. Chem.* 267:963–7, 1992; Wu et al., *J. Biol. Chem.* 263:14621–4, 1988.

Antisense methodology can be used to inhibit z219c gene transcription, such as to inhibit cell proliferation in vivo. Polynucleotides that are complementary to a segment of a z219c-encoding polynucleotide (e.g., a polynucleotide as set forth in SEQ ID NO:1) are designed to bind to z219c-encoding mRNA and to inhibit translation of such mRNA. Such antisense polynucleotides are used to inhibit expression of z219c polypeptide-encoding genes in cell culture or in a subject Polynucleotides of the present invention are also used to detect abnormalities on human chromosome 3 associated with disease or other human traits. The polynucleotides of the present invention map to the 3p21.1-p13 region on human chromosome 3. Some chemokine receptors (CMKBR1, 2 and 5) as well as a marker associated with pancreatic cancer map to this region of human chromosome 3. z219c maps 230.61 cR__3000 from the top of the human chromosome 3 linkage group on the WICGR radiation hybrid map. Proximal and distal framework markers were WI-6691 and (D3S3117) and D3S1313, respectively. The user of surrounding markers positions Z219c in the 3p21.1-p13 region on the integrated LDB chromosome 3 map.

The present invention also provides reagents which will find use in diagnostic applications. For example, the z219c gene, a probe comprising z219c DNA or RNA or a subsequence thereof can be used to determine if the z219c gene is present on chromosome 3 or if a mutation has occurred. Detectable chromosomal aberrations at the z219c gene locus include but are not limited to aneuploidy, gene copy number changes, insertions, deletions, restriction site changes and rearrangements. Such aberrations can be detected using polynucleotides of the present invention by employing molecular genetic techniques, such as restriction fragment length polymorphism (RFLP) analysis, short tandem repeat (STR) analysis employing PCR techniques, and other genetic linkage analysis techniques known in the art (Sambrook et al., ibid.; Ausubel, et. al., ibid.; Marian, A. J., Chest, 108: 255–265, 1995). These methods can be employed to use z219c polynucleotides to detect abnormalities on human chromosome 3, such as those described below.

The precise knowledge of a gene's position can be useful for a number of purposes, including: 1) determining if a sequence is part of an existing contig and obtaining additional surrounding genetic sequences in various forms, such as YACs, BACs or cDNA clones; 2) providing a possible candidate gene for an inheritable disease which shows linkage to the same chromosomal region; and 3) cross-referencing model organisms, such as mouse, which may aid in determining what function a particular gene has.

The z219c gene is located at the 3p21.1-p13 region of chromosome 3. Several genes of known function map to this region. For example, arginine-rich protein (ARP) maps to 3p21.1. Deletions in ARP are associated with solid tumors of various types, and deletions and mutations at codon 50 are observed in pancreatic tumors (Shridhar, R. et al, Cancer Res., 56:5576–5578, 1996; Shridhar, V. et al, Oncogene, 12:1931–1939, 1996; Shridhar, V. et al, Oncogene, 14:2213–2216, 1997). Moreover, z219c polynucleotide probes can be used to detect abnormalities or genotypes associated with these ARP defects. In addition, z219c polynucleotide probes can be used to detect abnormalities or genotypes associated with neurosensory nonsundromic recessive deafness (DFNB6) which maps to 3p21-p14 (Fukushima, K. et al., Genome Res. 5:305–308, 1995; Petit, C., Nature Genet. 14:385–391, 1996). Moreover, amongst other genetic loci, those for familial nonpolyposis type 2 colorectal cancer (3p21.3), Larsen syndrome (3p21.1-p14.1), and nonketotic type II hyperglycinemia (3p21.2-p21.1), all manifest themselves in human disease states as well as map to this region of the human genome. See the Online Mendellian Inheritance of Man (OMIM) gene map, and references therein, for this region of chromosome 3 on a publicly available WWW server (http://www3.ncbi.nlm.nih.gov/htbin-post/Omim/getmap?chromosome=3p21.1). All of these serve as possible candidate genes for an inheritable disease which show linkage to the same chromosomal region as the z219c gene.

Similarly, defects in the z219c gene itself may result in a heritable human disease state. Molecules of the present invention, such as the polypeptides, antagonists, agonists, polynucleotides and antibodies of the present invention would aid in the detection, diagnosis prevention, and treatment associated with a z219c genetic defect.

Mice engineered to express the z219c gene, referred to as "transgenic mice," and mice that exhibit a complete absence of z219c gene function, referred to as "knockout mice," may also be generated (Snouwaert et al., Science 257:1083, 1992; Lowell et al., Nature 366:740–42, 1993; Capecchi, M. R., Science 244: 1288–1292, 1989; Palmiter, R. D. et al. Annu Rev Genet. 20: 465–499, 1986). For example, transgenic mice that over-express z219c, either ubiquitously or under a tissue-specific or tissue-restricted promoter can be used to ask whether over-expression causes a phenotype. For example, over-expression of a wild-type z219c polypeptide, polypeptide fragment or a mutant thereof may alter normal cellular processes, resulting in a phenotype that identifies a tissue in which z219c expression is functionally relevant and may indicate a therapeutic target for the z219c, its agonists or antagonists. For example, a preferred transgenic mouse to engineer is one that over-expresses the mature z219c polypeptide. Moreover, such over-expression may result in a phenotype that shows similarity with human diseases. Similarly, knockout z219c mice can be used to determine where z219c is absolutely required in vivo. The phenotype of knockout mice is predictive of the in vivo effects of that a z219c antagonist, such as those described herein, may have. The human z219c cDNA can be used to isolate murine z219c mRNA, cDNA and genomic DNA, which are subsequently used to generate knockout mice. These mice may be employed to study the z219c gene and the protein encoded thereby in an in vivo system, and can be used as in vivo models for corresponding human diseases. Moreover, transgenic mice expression of z219c antisense polynucleotides or ribozymes directed against z219c, described herein, can be used analogously to knockout mice described above.

Other diagnostic applications using z219c can be employed. For example, the z219c gene, a probe comprising z219c DNA or RNA or a subsequence thereof can be used to determine if the z219c gene is expressed differently in diseased tissues. For example, among other diseases, z219c may be expressed in certain pancreatic, prostatic, intestinal, throat and lung cancers, or other diseases associated with those tissues. In the alternative, z219c expression in certain tissues may be decreased in certain disease states relative to normal.

Within another aspect of the present invention there is provided a pharmaceutical composition comprising purified z219c polypeptide in combination with a pharmaceutically acceptable vehicle. This pharmaceutical composition will be used to modulate energy balance in mammals or to protect epithelial cells from injury.

With regard to modulating energy balance, z219c polypeptide modulate cellular metabolic reactions. Such metabolic reactions include adipogenesis, gluconeogenesis, glycogenolysis, lipogenesis, glucose uptake, protein synthesis, thermogenesis, oxygen utilization and the like. The expression pattern of z219c polypeptide shows expression in epithelial cell tissues. With regard to epithelial cell protection, z219c polypeptide may be used in organ preservation, for cryopreservation, for surgical pretreatment to prevent injury due to ischemia and/or inflammation or in like procedures. In this regard, z219c polypeptides may find utility in modulating nutrient uptake, as demonstrated, for example, by 2-deoxy-glucose uptake in the brain or the like.

The z219c polypeptides may modulate mammalian energy balance. The expression pattern of z219c polypeptide shows expression in pancreas. Among other methods known in the art or described herein, mammalian energy balance may be evaluated by monitoring one or more of the following metabolic functions: adipogenesis, gluconeogenesis, glycogenolysis, lipogenesis, glucose uptake, protein synthesis, thermogenesis, oxygen utilization or the like. These metabolic functions are monitored by techniques (assays or animal models) known to one of ordinary skill in the art, as is more fully set forth below. For example, the glucoregulatory effects of insulin are predominantly exerted in the liver, skeletal muscle and adipose tissue. Insulin binds to its cellular receptor in these three tissues and initiates tissue-specific actions that result in, for example, the inhibition of glucose production and the stimulation of glucose utilization. In the liver, insulin stimulates glucose uptake and inhibits gluconeogenesis and glycogeneolysis. In skeletal muscle and adipose tissue, insulin acts to stimulate the uptake, storage and utilization of glucose.

Moreover, pancreatic expression of z219c polypeptide suggests the pharmaceutical compositions of the present invention may be useful in prevention or treatment of pancreatic disorders associated with pathological regulation of the expansion of neurocrine and exocrine cells in the pancreas, such as IDDM, pancreatic cancer or the like. Pharmaceutical compositions of the present invention may also be involved in prevention or treatment of pancreatic conditions characterized by dysfunction associated with pathological regulation of blood glucose levels, insulin resistance or digestive function.

Art-recognized methods exist for monitoring all of the metabolic functions recited above. Thus, one of ordinary skill in the art is able to evaluate z219c polypeptides, fragments, fusion proteins, antibodies, agonists and antagonists for metabolic modulating functions. Exemplary modulating techniques are set forth below.

Adipogenesis, gluconeogenesis and glycogenolysis are interrelated components of mammalian energy balance, which may be evaluated by known techniques using, for example, ob/ob mice or db/db mice. The ob/ob mice are inbred mice that are homozygous for an inactivating mutation of the ob (obese) locus. Such ob/ob mice are hyperphagic and hypometabolic, and are believed to be deficient in production of circulating OB protein. The db/db mice are inbred mice that are homozygous for an inactivating mutation at the db (diabetes) locus. The db/db mice display a phenotype similar to that of ob/ob mice, except db/db mice display a more severe diabetic phenotype. Such db/db mice are believed to be resistant to the effects of circulating OB protein. Also, various in vitro methods of assessing these parameters are known in the art.

Insulin-stimulated lipogenesis, for example, may be monitored by measuring the incorporation of $^{14}$C-acetate into triglyceride (Mackall et al. *J. Biol. Chem.* 251:6462–6464, 1976) or triglyceride accumulation (Kletzien et al., *Mol. Pharmacol.* 41:393–398, 1992).

Glucose uptake may be evaluated, for example, in an assay for insulin-stimulated glucose transport. Non-transfected, differentiated L6 myotubes (maintained in the absence of G418) are placed in DMEM containing 1 g/l glucose, 0.5 or 1.0% BSA, 20 mM Hepes, and 2 mM glutamine. After two to five hours of culture, the medium is replaced with fresh, glucose-free DMEM containing 0.5 or 1.0% BSA, 20 mM Hepes, 1 mM pyruvate, and 2 mM glutamine. Appropriate concentrations of insulin or IGF-1, or a dilution series of the test substance, are added, and the cells are incubated for 20–30 minutes. $^3$H or $^{14}$C-labeled deoxyglucose is added to ≈50 M final concentration, and the cells are incubated for approximately 10–30 minutes. The cells are then quickly rinsed with cold buffer (e.g. PBS), then lysed with a suitable lysing agent (e.g. 1% SDS or 1 N NaOH). The cell lysate is then evaluated by counting in a scintillation counter. Cell-associated radioactivity is taken as a measure of glucose transport after subtracting non-specific binding as determined by incubating cells in the presence of cytochalasin b, an inhibitor of glucose transport. Other methods include those described by, for example, Manchester et al., *Am. J. Physiol.* 266 (*Endocrinol. Metab.* 29): E326–E333, 1994 (insulin-stimulated glucose transport).

Protein synthesis may be evaluated, for example, by comparing precipitation of $^{35}$S-methionine-labeled proteins following incubation of the test cells with $^{35}$S-methionine and $^{35}$S-methionine and a putative modulator of protein synthesis.

Thermogenesis may be evaluated as described by B. Stanley in *The Biology of Neuropeptide Y and Related Peptides,* W. Colmers and C. Wahlestedt (eds.), Humana Press, Ottawa, 1993, pp. 457–509; C. Billington et al., *Am. J. Physiol.* 260:R321, 1991; N. Zarjevski et al., *Endocrinology* 133:1753, 1993; C. Billington et al., *Am. J. Physiol.* 266:R1765, 1994; Heller et al., *Am. J. Physiol.* 252(4 Pt 2): R661–7, 1987; and Heller et al., *Am. J. Physiol.* 245(3): R321–8, 1983. Also, metabolic rate, which may be measured by a variety of techniques, is an indirect measurement of thermogenesis.

Oxygen utilization may be evaluated as described by Heller et al., *Pflugers Arch* 369(1): 55–9, 1977. This method also involved an analysis of hypothalmic temperature and metabolic heat production. Oxygen utilization and thermoregulation have also been evaluated in humans as described by Haskell et al., *J. Appl. Physiol.* 51(4): 948–54, 1981.

z219c polypeptide is expressed in the small intestine, pancreas and trachea. Secreted products from these organs can play important roles in the maintenance of normal gastric epithelium and function. Thus, z219c polypeptide pharmaceutical compositions of the present invention may also be useful in prevention or treatment of gastric mucositis. Mucositis is manifested by the damage and loss of integrity of the oral and gastric epithelium. Such damage often provides a microbial port of entry leading to sepsis. Mucositis is often induced by chemotherapy and radiation therapy, and is often a dose-limiting side effect as well as a cause of mortality in cancer patients undergoing such treatment. The z219c polypeptides of the present invention may provide protection against gastric mucositis, analogous to some growth factors and cytokines, for example, interleukin-11 (Orazi, A. et al., *Lab. Invest.* 75:33–42, 1996). The effect of z219c prevention or treatment of gastric mucositis can be measured in in vivo animal models, for example, the Syrian hamster model or in murine models using methods described in the art (Sonis, S. T. et al., *Oral Surg. Oral Med. Oral Pathol.* 69:437–443, 1990; Farrell, C. L. et al., *Cancer Res.* 58:933–939, 1998; Orazi, A. et al., supra.).

The z219c polypeptide is expressd in the small intestine. Thus, z219c polypeptide pharmaceutical compositions of the present invention may also be useful in prevention or treatment of digestive disorders in the GI tract, such as disorders associated with pathological secretory cell expansion or differentiation. Assays and animal models are known in the art for monitoring such expansion or differentiation and for evaluating z219c polypeptide, fragment, fusion protein, antibody, agonist or antagonist in the prevention or treatment thereof.

Moreover, trefoil factors in the intestine are known to be involved in mucosal stabilization in the gut and repair processes associated with acute injury, particularly epithelial restitution (Poulsom R., *Bail. Clin. Gastro.,* 10; 113–134, 1996; Sands, B. E., and Podolsky, D. K., *Annu. Rev. Physiol.,* 58; 253–273, 1996. Also, trefoil protein appear to have a role in healing wounds caused by interstinal inflammatory diseases, and resisting microbial invasion via mucosal secretion involving (Palut, A. G., *New Eng. J. Med.,* 336; 5-6-507, 1997; Playford, R. J., *J. Royal Coll. Phys. London,* 31; 37–41, 1997) Epidermal growth factor (EGF)

receptor ligands may play a role in enhancing trefoil activity in the gut; however, repair of mucosal injury is not dependent in the main endogenous EGF receptor ligand in the gut, TNF-a, suggesting a role of other undiscovered ligands (Cook, G. A., et al., *Am Physiol. Soc., G*1540–G1549, 1997). For example, the z219c polypeptides may serve as such ligand, regulatory protein or other factor in the trefoil pathway, and hence play an important therapeutic role in epithelium.

Also, z219c polypeptide is expressed in the pancreas and its function there may be independent of gastrointestinal function. Thus, z219c polypeptide pharmaceutical compositions of the present invention may be useful in prevention or treatment of pancreatic disorders associated with pathological regulation of the expansion of neuroendocrine and exocrine cells in the pancreas, such as IDDM, pancreatic cancer, pathological regulation of blood glucose levels, insulin resistance or digestion function.

The z219c polypetide of the present invention may act in the neuroendocrine/exocrine cell fate decision pathway and is therefore capable of regulating the expansion of neuroendocrine and exocrine cells in the pancreas. One such regulatory use is that islet cell regeneration. Also, it has been hypothesized that the autoimmunity that triggers IDDM starts in utero, and z219c polypeptide is a developmental gene involved in cell partitioning. Assays and animal models are known in the art for monitoring the exocrine/neuroendocrine cell lineage decision, for observing pancreatic cell balance and for evaluating z219c polypeptide, fragment, fusion protein, antibody, agonist or antagonist in the prevention or treatment of the conditions set forth above.

Within another aspect of the present invention there is provided a pharmaceutical composition comprising purified z219c polypeptide in combination with a pharmaceutically acceptable vehicle. Such pharmaceutical compositions may be administered to prevent or treat salivary gland dysfunction. Such prevention or treatment may be directed to digestive dysfunction, such as a deficiency in starch breakdown capability or efficiency, wound healing dysfunction, inadequate saliva production or composition of mucosal integrity breakdown. Z219c polypeptides may also have an anti-microbial function. Also, expression of z219c polypeptide at a relatively high level in trachea may indicate a role for z219c polypeptides in prevention or treatment of destructive lung disease. Examples of pathological conditions, characterized by one or more of the aforementioned criteria, include xerostomia, sarcoidosis, dental caries, osteomyelitis, oral candidiasis, buccal mucosa infections, chronic inflammation (Sjogren's syndrome), mumps, chronic bronchitis, adult respiratory distress syndrome (ARDS), sudden infant death syndrome (SIDS), salivary gland carcinoma, pneumocystic carinii (particularly as associated with AIDS patients), cystic fibrosis, emphysema and the like.

Evaluation of z219c polypeptide involvement in such conditions may be conducted using in vivo or in vitro methods that are known to those of ordinary skill in the art. For example, bronchoalveolar lavage may be employed in the assessment of destructive lung diseases, such as pulmonary emphysema, chronic bronchitis, cystic fibrosis, ARDS and the like. See, for example, Luisetti et al., *Respiration* 59 (suppl. 1) 24–27, 1992. Salivary gland, lacrimal gland and labial salivary gland biopsies may be employed in the evaluation of xerostomia. See, for example, Matsumoto et al., *J. Clin. Invest.* 97(8): 1969–77, 1996. This calcium channel dependent condition has also been evaluated using fura-2 assays of intracellular calcium ion concentration, as described in Seagrave et al., *Archs. Oral Biol.* 41(5): 425–30, 1996. Alymphoplasia (aly) mice are a useful animal model for systemic Sjogren's syndrome, an autoimmune disease characterized by lymphocytic infiltration into the lachrymal and salivary glands, leading to symptomatic dry eyes and mouth. See, for example, Furukawa et al., *British Journal of Rheumatology* 35: 1223–30, 1996.

For pharmaceutical use, the proteins of the present invention are formulated for parenteral, particularly intravenous or subcutaneous, delivery according to conventional methods. Intravenous administration will be by bolus injection or infusion over a typical period of one to several hours. For applications for which local effects are preferred, such as for influencing the formation of certain types of mature cells from localized (e.g., pancreatic) stem cells, formulations designed for local administration are preferred. Such pharmaceutical compostions are amenable, for example, to implantation or other local delivery method and may additionally be formulated for sustained release. Formulation of pharmaceutical compositions for a variety of modes of administration is within the ordinary skill in the art. In general, pharmaceutical formulations will include a z219c protein in combination with a pharmaceutically acceptable vehicle, such as saline, buffered saline, 5% dextrose in water or the like. Formulations may further include one or more excipients, preservatives, solubilizers, buffering agents, albumin to prevent protein loss on vial surfaces, etc. Methods of formulation are well known in the art and are disclosed, for example, in Remington: *The Science and Practice of Pharmacy,* Gennaro, ed., Mack Publishing Co., Easton, Pa., 19th ed., 1995. Therapeutic doses will generally be determined by the clinician according to accepted standards, taking into account the nature and severity of the condition to be treated, patient traits, etc. Determination of dose is within the level of ordinary skill in the art. The proteins may be administered for acute treatment, over one week or less, often over a period of one to three days or may be used in chronic treatment, over several months or years.

The invention is further illustrated by the following non-limiting examples.

EXAMPLES

Example 1

Extension of EST Sequence

Scanning of a translated DNA database using human proteins containing a signal sequence as a query resulted in identification of an expressed sequence tag (EST) sequence found to be homologous to murine EF-7, in the 2–19 family and designated z219c.

Confirmation of the EST sequence was made by sequence analyses of the cDNA from which the EST originated. This cDNA was contained in a plasmid, and was excised using Eco RI and Not I cloning sites. A cDNA clone was obtained and sequenced using the following primers: ZC 694 (SEQ ID NO:9) and ZC 695 (SEQ ID NO:10). The clone appeared complete in the 3' prime end but incomplete in the 5' prime end.

A 5' RACE (rapid amplification of cDNA ends) reaction was used to generate additional cDNA sequence. A stomach "marathon ready" cDNA library was used as template with oligonucleotide ZC 13,978 (SEQ ID NO:11) and the marathon primer AP-1 (Clontech) in a PCR reaction performed as follows: 30 cycles at 94° C. for 30 seconds, 68° C. for 20 seconds, and 72° C. for 30 seconds; followed by one cycle at 72° C. for 5 minutes. The product was diluted 1:50 and used as a template in a 5' nested RACE with oligonucleotide ZC 15,228 (SEQ ID NO:12) and the marathon primer AP-2 (Clontech) for 25 cycles under the same conditions disclosed above. Gel electrophoresis of the product resulted in two distinct bands between 350 and 400 bp. The bands were isolated and gel extracted (QIAEX II, Qiagen). The fragments were sequenced and analysis of the smaller fragment indicated homology to the 5' end of z219c and extension of the sequence to an initiating MET. The sequence analyses revealed that the cDNA encompassed the entire coding region of the DNA encoding z219c.

Example 2

Tissue Distribution

Northern blots were performed using Human Multiple Tissue and Master Dot Blots from Clontech (Palo Alto, Calif.). A probe was obtained by PCR using primers ZC 14,067 (SEQ ID NO:13) and ZC 14,068 (SEQ ID NO:14) and the z219c clone as a template. A 452 bp fragment internal to the gene was selected for amplification. The conditions for PCR was as follows: 1 cycle at 94° C. for 5 minutes; 30 cycles at 94° C. for 30 seconds, 60° C. for 30 seconds; followed by a 4° C. degree hold. A sample of the resulting product was run on a gel to verify product size and purity. A band corresponding to the target DNA was cut out and gel purified with a QIAquick Gel Extraction Kit (QIAGEN INC. Chatsworth Calif.) and then radioactively labeled using the random priming REDIPRIME DNA labeling system (Amersham, Arlington Heights, Ill.) according to the manufacturer's specifications. The probe was purified using a NUCTRAP push column (Stratagene Cloning Systems, La Jolla, Calif.). EXPRESSHYB (Clontech) solution was used for prehybridization and as a hybridizing solution for the Northern blots. Hybridization took place overnight at 50° C., and the blots were then washed in 2× SSC and 0.05% SDS at room temperature, followed by a wash in 1× SSC and 0.1% SDS at 55° C., followed by a wash in 0.1× SSC, 0.1% SDS at 55° C.

One transcript size was observed on the MTNs at ~1 kb. Signal intensity was highest in trachea with strong signals in stomach and colon, and moderately strong signals in pancreas, prostate and small intestine. The Dot blot showed an additional strong signal in salivary gland with faint signals in kidney, fetal kidney, fetal liver, fetal spleen, fetal thymus, and fetal lung.

Example 3

PCR-Based Chromosomal Mapping of the z219c Gene

Z219c was mapped to chromosome 3 using the commercially available "GeneBridge 4 Radiation Hybrid Panel" (Research Genetics, Inc.). The GeneBridge 4 Radiation Hybrid Panel contains DNAs from each of 93 radiation hybrid clones, plus two control DNAs (the HFL donor and the A23 recipient). A publicly available WWW server (http://www-genome.wi.mit.edu/cgi-bin/contig/rhmapper.pl) allows mapping relative to the Whitehead Institute/MIT Center for Genome Research's radiation hybrid map of the human genome (the "WICGR" radiation hybrid map) which was constructed with the GeneBridge 4 Radiation Hybrid Panel.

For the mapping of Z219c with the "GeneBridge 4 Rh Panel", 20 µl reactions were set up in a 96-well microtiter plate (Stratagene, La Jolla, Calif.) and used in a "RoboCycler Gradient 96" thermal cycler (Strategene). Each of the 95 PCR reactions consisted of 2 µl 10× KlenTaq PCR reaction buffer (Clontech Laboratories, Inc., Palo Alto, Calif.), 1.6 µl dNTPs mix (2.5 mM each, PERKIN-ELMER, Foster City, Calif.), 1 µl sense primer, ZC 14,869 (SEQ ID NO:15) 1 µl antisense primer, ZC 14,868 (SEQ ID NO:16), 2 µl "Redi-Load" (Research Genetics, Inc., Huntsville, Ala.), 0.4 µl 50× Advantage KlenTaq Polymerase Mix (Clontech Laboratories, Inc.), 25 ng of DNA from an individual hybrid clone or control and ddH$_2$O for a total volume of 20 µl. The reactions were overlaid with an equal amount of mineral oil and sealed. The PCR cycler conditions were as follows: an initial 1 cycle 5 minute denaturation at 95° C., 35 cycles of a 1 minute denaturation at 95° C., 1 minute annealing at 60° C. and 1.5 minute extension at 72° C., followed by a final 1 cycle extension of 7 minutes at 72° C. The reactions were separated by electrophoresis on a 2% agarose gel (Life Technologies, Gaithersburg, Md.).

The results showed that z219c maps 230.61 cr_3000 from the top of the human chromsome 3 linkage group on the WICGR radiation hybrid map. Proximal and distal framework markers were WI-6691 (D3S3117) and D3S1313, respectively. The use of surrounding markers positions Z219c in the 3p21.1-p13 region on the integrated LDB chromosome 3 map (The Genetic Location Database, University of Southampton, WWW server: http://cedar.genetics.soton.ac.uk/public_html/).

From the foregoing, it will be appreciated that, although specific embodiments of the invention have been described herein for purpose of illustration, various modifications may be made without deviating from the spirit and scope of the invention. Accordingly, the invention is not limited except as by the appended claims.

What is claimed is:

1. A DNA construct encoding a fusion protein, the DNA construct comprising:

a first DNA segment encoding a polypeptide comprising a sequence of amino acid residues 1 (Met) through 21 (Met) of SEQ ID NO:2; and a second DNA segment encoding an additional polypeptide, wherein the first and second DNA segments are connected in-frame; and encode the fusion protein.

2. A vector comprising the following operably linked elements:

a transcription promoter, a DNA construct according to claim 1; and a transcription terminator, wherein the transcription promoter is operably linked to the DNA construct, and the DNA construct is operably linked to the transcription terminator.

3. A cell into which has been introduced a vector according to claim 2.

* * * * *

SEQUENCE LISTING

```
<160> NUMBER OF SEQ ID NOS: 19

<210> SEQ ID NO 1
<211> LENGTH: 1221
<212> TYPE: DNA
<213> ORGANISM: Homo sapiens
<220> FEATURE:
<221> NAME/KEY: CDS
<222> LOCATION: (222)...(889)
```

<400> SEQUENCE: 1

```
cgcccgggca ggttgcatct agaggagggc cgtctgtgag ccactacccc tccagcaact    60 ggaggtggg actgtcagaa gctggcccag ggtggtggtc agctgggtca gggacctacg   120
gcacctgctg gaccacctcg ccttctccat cgaagcaggg aagtgggagc ctcgagccct   180
cgggtggaag ctgaccccaa gccacccttc acctggacag g atg aga gtg tca ggt   236
                                              Met Arg Val Ser Gly
                                                1               5 gtg ctt cgc ctc ctg gcc ctc atc ttt gcc ata gtc acg aca tgg atg    284
Val Leu Arg Leu Leu Ala Leu Ile Phe Ala Ile Val Thr Thr Trp Met
         10                  15                  20 ttt att cga agc tac atg agc ttc agc atg aaa acc atc cgt ctg cca    332
Phe Ile Arg Ser Tyr Met Ser Phe Ser Met Lys Thr Ile Arg Leu Pro
             25                  30                  35 cgc tgg ctg gcc tcg ccc acc aag gag atc cag gtt aaa aag tac aag    380
Arg Trp Leu Ala Ser Pro Thr Lys Glu Ile Gln Val Lys Lys Tyr Lys
         40                  45                  50 tgt ggc ctc atc aag ccc tgc cca gcc aac tac ttt gcg ttt aaa atc    428
Cys Gly Leu Ile Lys Pro Cys Pro Ala Asn Tyr Phe Ala Phe Lys Ile
 55                  60                  65 tgc agt ggg gcc gcc aac gtc gtg ggc cct act atg tgc ttt gaa gac    476
Cys Ser Gly Ala Ala Asn Val Val Gly Pro Thr Met Cys Phe Glu Asp
 70                  75                  80                  85 cgc atg atc atg agt cct gtg aaa aac aat gtg ggc aga ggc cta aac    524
Arg Met Ile Met Ser Pro Val Lys Asn Asn Val Gly Arg Gly Leu Asn
             90                  95                 100 atc gcc ctg gtg aat gga acc acg gga gct gtg ctg gga cag aag gca    572
Ile Ala Leu Val Asn Gly Thr Thr Gly Ala Val Leu Gly Gln Lys Ala
            105                 110                 115 ttt gac atg tac tct gga gat gtt atg cac cta gtg aaa ttc ctt aaa    620
Phe Asp Met Tyr Ser Gly Asp Val Met His Leu Val Lys Phe Leu Lys
        120                 125                 130 gaa att ccg ggg ggt gca ctg gtg ctg gtg gcc tcc tac gac gat cca    668
Glu Ile Pro Gly Gly Ala Leu Val Leu Val Ala Ser Tyr Asp Asp Pro
    135                 140                 145 ggg acc aaa atg aac gat gaa agc agg aaa ctc ttc tct gac ttg ggg    716
Gly Thr Lys Met Asn Asp Glu Ser Arg Lys Leu Phe Ser Asp Leu Gly
150                 155                 160                 165 agt tcc tac gca aaa caa ctg ggc ttc cgg gac agc tgg gtc ttc ata    764
Ser Ser Tyr Ala Lys Gln Leu Gly Phe Arg Asp Ser Trp Val Phe Ile
                170                 175                 180 gga gcc aaa gac ctc agg ggt aaa agc ccc ttt gag cag ttc tta aag    812
Gly Ala Lys Asp Leu Arg Gly Lys Ser Pro Phe Glu Gln Phe Leu Lys
            185                 190                 195 aac agc cca gac aca aac aaa tac gag gga tgg cca gag ctg ctg gag    860
Asn Ser Pro Asp Thr Asn Lys Tyr Glu Gly Trp Pro Glu Leu Leu Glu
        200                 205                 210 atg gag ggc tgc atg ccc ccg aag cca tt ttagggtggc tgtggctctt      909
Met Glu Gly Cys Met Pro Pro Lys Pro
    215                 220 cctcagccag gggcctgaag aagctcctgc ctgacttagg agtcagagcc cggcagggc   969 tgaggaggag gagcagggg tgctgcgtgg aaggtgctgc aggtccttgc acgctgtgtc  1029
gcgcctctcc tcctcggaaa cagaaccctc ccacagcaca tcctacccgg aagaccagcc  1089
tcagagggtc cttctggaac cagctgtctc tggagagaat ggggtgcttt cgtcagggac  1149
tgctgacggc tggtcctgag gaaggacaaa ctgcccagac ttgagcccaa ttaaatttta  1209
```

```
tttttgctgg ta                                                        1221
```

<210> SEQ ID NO 2
<211> LENGTH: 223
<212> TYPE: PRT
<213> ORGANISM: Homo sapiens
<400> SEQUENCE: 2

```
Met Arg Val Ser Gly Val Leu Arg Leu Leu Ala Leu Ile Phe Ala Ile
 1               5                  10                  15

Val Thr Thr Trp Met Phe Ile Arg Ser Tyr Met Ser Phe Ser Met Lys
            20                  25                  30

Thr Ile Arg Leu Pro Arg Trp Leu Ala Ser Pro Thr Lys Glu Ile Gln
        35                  40                  45

Val Lys Lys Tyr Lys Cys Gly Leu Ile Lys Pro Cys Pro Ala Asn Tyr
    50                  55                  60

Phe Ala Phe Lys Ile Cys Ser Gly Ala Ala Asn Val Val Gly Pro Thr
65                  70                  75                  80

Met Cys Phe Glu Asp Arg Met Ile Met Ser Pro Val Lys Asn Asn Val
                85                  90                  95

Gly Arg Gly Leu Asn Ile Ala Leu Val Asn Gly Thr Thr Gly Ala Val
            100                 105                 110

Leu Gly Gln Lys Ala Phe Asp Met Tyr Ser Gly Asp Val Met His Leu
        115                 120                 125

Val Lys Phe Leu Lys Glu Ile Pro Gly Gly Ala Leu Val Leu Val Ala
    130                 135                 140

Ser Tyr Asp Asp Pro Gly Thr Lys Met Asn Asp Glu Ser Arg Lys Leu
145                 150                 155                 160

Phe Ser Asp Leu Gly Ser Ser Tyr Ala Lys Gln Leu Gly Phe Arg Asp
                165                 170                 175

Ser Trp Val Phe Ile Gly Ala Lys Asp Leu Arg Gly Lys Ser Pro Phe
            180                 185                 190

Glu Gln Phe Leu Lys Asn Ser Pro Asp Thr Asn Lys Tyr Glu Gly Trp
        195                 200                 205

Pro Glu Leu Leu Glu Met Glu Gly Cys Met Pro Pro Lys Pro Phe
    210                 215                 220
```

<210> SEQ ID NO 3
<211> LENGTH: 3
<212> TYPE: PRT
<213> ORGANISM: Artificial Sequence
<220> FEATURE:
<223> OTHER INFORMATION: Z219c polypeptide Motif 1

<400> SEQUENCE: 3

```
Phe Asp Met
 1
```

<210> SEQ ID NO 4
<211> LENGTH: 3
<212> TYPE: PRT
<213> ORGANISM: Artificial Sequence
<220> FEATURE:
<223> OTHER INFORMATION: Z219c polypeptide Motif 2

<400> SEQUENCE: 4

```
Tyr Asp Asp
 1
```

-continued

<210> SEQ ID NO 5
<211> LENGTH: 3
<212> TYPE: PRT
<213> ORGANISM: Artificial Sequence
<220> FEATURE:
<223> OTHER INFORMATION: Z219c polypeptide Motif 3

<400> SEQUENCE: 5

Leu Gly Ser
1

<210> SEQ ID NO 6
<211> LENGTH: 3
<212> TYPE: PRT
<213> ORGANISM: Artificial Sequence
<220> FEATURE:
<223> OTHER INFORMATION: Z219c polypeptide Motif 4

<400> SEQUENCE: 6

Trp Val Phe
1

<210> SEQ ID NO 7
<211> LENGTH: 3
<212> TYPE: PRT
<213> ORGANISM: Artificial Sequence
<220> FEATURE:
<223> OTHER INFORMATION: Z219c polypeptide Motif 5

<400> SEQUENCE: 7

Glu Gly Cys
1

<210> SEQ ID NO 8
<211> LENGTH: 669
<212> TYPE: DNA
<213> ORGANISM: Artificial Sequence
<220> FEATURE:
<223> OTHER INFORMATION: Degenerate polynucleotide sequence of z219c
<220> FEATURE:
<221> NAME/KEY: variation
<222> LOCATION: (0)...(0)
<223> OTHER INFORMATION: N is any nucleotide

<400> SEQUENCE: 8
atgmgngtnw snggngtnyt nmgnytnytn gcnytnatht tygcnathgt nacnacntgg 60
atgttyathm gnwsntayat gwsnttywsn atgaaracna thmgnytncc nmgntggytn 120
gcnwsnccna cnaargarat hcargtnaar aartayaart gyggnytnat haarccntgy 180
ccngcnaayt ayttygcntt yaarathtgy wsnggngcng cnaaygtngt nggnccnacn 240
atgtgyttyg argaymgnat gathatgwsn ccngtnaara ayaaygtngg nmgnggnytn 300
aayathgcny tngtnaaygg nacnacnggn gcngtnytng gncaraargc nttygayatg 360
taywsnggng aygtnatgca yytngtnaar ttyytnaarg arathccngg nggngcnytn 420
gtnytngtng cnwsntayga ygayccnggn acnaaratga aygaygarws nmgnaarytn 480
ttywsngayy tnggnwsnws ntaygcnaar carytnggnt tymgngayws ntgggtntty 540
athggngcna argayytnmg nggnaarwsn ccnttygarc arttyytnaa raaywsnccn 600
gayacnaaya artaygargg ntggccngar ytnytngara tggarggntg yatgccnccn 660 aarccntty 669

<210> SEQ ID NO 9
<211> LENGTH: 20

```
<212> TYPE: DNA
<213> ORGANISM: Artificial Sequence
<220> FEATURE:
<223> OTHER INFORMATION: Oligonucleotide primer ZC694

<400> SEQUENCE: 9
taatacgact cactataggg                                              20

<210> SEQ ID NO 10
<211> LENGTH: 19
<212> TYPE: DNA
<213> ORGANISM: Artificial Sequence
<220> FEATURE:
<223> OTHER INFORMATION: Oligonucleotide primer ZC695

<400> SEQUENCE: 10
gatttaggtg acactatag                                               19

<210> SEQ ID NO 11
<211> LENGTH: 25
<212> TYPE: DNA
<213> ORGANISM: Artificial Sequence
<220> FEATURE:
<223> OTHER INFORMATION: Oligonucleotide primer ZC13978

<400> SEQUENCE: 11
ggcggcccca ctgcagattt taaac                                        25

<210> SEQ ID NO 12
<211> LENGTH: 23
<212> TYPE: DNA
<213> ORGANISM: Artificial Sequence
<220> FEATURE:
<223> OTHER INFORMATION: Oligonucleotide primer ZC15288

<400> SEQUENCE: 12
ttggctgggc agggcttgat gag                                          23

<210> SEQ ID NO 13
<211> LENGTH: 21
<212> TYPE: DNA
<213> ORGANISM: Artificial Sequence
<220> FEATURE:
<223> OTHER INFORMATION: Oligonucleotide primer ZC14067

<400> SEQUENCE: 13
tggccatccc tcgtatttgt t                                            21

<210> SEQ ID NO 14
<211> LENGTH: 21
<212> TYPE: DNA
<213> ORGANISM: Artificial Sequence
<220> FEATURE:
<223> OTHER INFORMATION: Oligonucleotide primer ZC14068

<400> SEQUENCE: 14
ccctgcccag ccaactactt t                                            21

<210> SEQ ID NO 15
<211> LENGTH: 21
<212> TYPE: DNA
<213> ORGANISM: Artificial Sequence
<220> FEATURE:
<223> OTHER INFORMATION: Oligonucleotide primer ZC14869

<400> SEQUENCE: 15
```

```
agcccagaca caaacaaata c                                          21
```

<210> SEQ ID NO 16
<211> LENGTH: 21
<212> TYPE: DNA
<213> ORGANISM: Artificial Sequence
<220> FEATURE:
<223> OTHER INFORMATION: Oligonucleotide primer ZC14868

<400> SEQUENCE: 16

```
tgccgggctc tgactcctaa g                                          21
```

<210> SEQ ID NO 17
<211> LENGTH: 115
<212> TYPE: PRT
<213> ORGANISM: Mus musculus

<400> SEQUENCE: 17

```
Thr Gly Gln Val Met Lys Lys Asp Ser Phe Asp Met Tyr Ser Gly Asp
 1               5                  10                  15

Pro Gln Leu Leu Leu Asn Phe Leu Thr Glu Ile Pro Asp Ser Thr Leu
            20                  25                  30

Val Leu Val Ala Ser Tyr Asp Asp Pro Gly Thr Lys Met Asn Asp Lys
        35                  40                  45

Ile Lys Thr Leu Phe Ser Asn Leu Gly Ser Ser Tyr Ala Lys Gln Leu
 50                  55                  60

Gly Phe Arg Asp Ser Trp Val Phe Val Gly Ala Lys Asp Leu Lys Ser
 65                  70                  75                  80

Lys Ser Pro Tyr Glu Gln Phe Leu Lys Asn Asn Pro Glu Thr Asn Lys
                85                  90                  95

Tyr Asp Gly Trp Pro Glu Leu Leu Glu Leu Gly Cys Val Pro Arg
            100                 105                 110

Lys Val Met
        115
```

<210> SEQ ID NO 18
<211> LENGTH: 230
<212> TYPE: PRT
<213> ORGANISM: Homo sapiens

<400> SEQUENCE: 18

```
Met Arg Leu Ala Gly Pro Leu Arg Ile Val Leu Val Val Ser Val
 1               5                  10                  15

Gly Val Thr Trp Ile Val Val Ser Ile Leu Leu Gly Pro Gly Ser
            20                  25                  30

Gly Phe Pro Arg Ile Gln Gln Leu Phe Thr Ser Pro Glu Ser Ser Val
        35                  40                  45

Thr Ala Ala Pro Arg Ala Arg Lys Tyr Lys Cys Gly Leu Pro Gln Pro
 50                  55                  60

Cys Pro Glu Glu His Leu Ala Phe Arg Val Val Ser Gly Ala Ala Asn
 65                  70                  75                  80

Val Ile Gly Pro Lys Ile Cys Leu Glu Asp Lys Met Leu Met Ser Ser
                85                  90                  95

Val Lys Asp Asn Val Gly Arg Gly Leu Asn Ile Ala Leu Val Asn Gly
            100                 105                 110

Val Ser Gly Glu Leu Ile Glu Ala Arg Ala Phe Asp Met Trp Ala Gly
        115                 120                 125

Asp Val Asn Asp Leu Leu Lys Phe Ile Arg Pro Leu His Glu Gly Thr
```

-continued

```
            130                 135                 140
Leu Val Phe Val Ala Ser Tyr Asp Asp Pro Ala Thr Lys Met Asn Glu
145                 150                 155                 160

Glu Thr Arg Lys Leu Phe Ser Glu Leu Gly Ser Arg Asn Ala Lys Glu
                165                 170                 175

Leu Ala Phe Arg Asp Ser Trp Val Phe Val Gly Ala Lys Gly Val Gln
                180                 185                 190

Asn Lys Ser Pro Phe Glu Gln His Val Lys Asn Ser Lys His Ser Asn
                195                 200                 205

Lys Tyr Glu Gly Cys Pro Glu Ala Leu Glu Met Glu Gly Cys Ile Pro
210                 215                 220

Arg Arg Ser Thr Ala Ser
225                 230

<210> SEQ ID NO 19
<211> LENGTH: 227
<212> TYPE: PRT
<213> ORGANISM: Homo sapiens

<400> SEQUENCE: 19

Met Arg Val Ala Gly Ala Ala Lys Leu Val Ala Val Ala Val Phe
 1                   5                  10                  15

Leu Leu Thr Phe Tyr Val Ile Ser Gln Val Phe Glu Ile Lys Met Asp
                 20                  25                  30

Ala Ser Leu Gly Asn Leu Phe Ala Arg Ser Ala Leu Asp Thr Ala Ala
                 35                  40                  45

Arg Ser Thr Lys Pro Pro Arg Tyr Lys Cys Gly Ile Ser Lys Ala Cys
 50                  55                  60

Pro Glu Lys His Phe Ala Phe Lys Met Ala Ser Gly Ala Ala Asn Val
 65                  70                  75                  80

Val Gly Pro Lys Ile Cys Leu Glu Asp Asn Val Leu Met Ser Gly Val
                 85                  90                  95

Lys Asn Asn Val Gly Arg Gly Ile Asn Val Ala Leu Ala Asn Gly Lys
                100                 105                 110

Thr Gly Glu Val Leu Asp Thr Lys Tyr Phe Asp Met Trp Gly Gly Asp
                115                 120                 125

Val Ala Pro Phe Ile Glu Phe Leu Lys Ala Ile Gln Asp Gly Thr Ile
                130                 135                 140

Val Leu Met Gly Thr Tyr Asp Asp Gly Ala Thr Lys Leu Asn Asp Glu
145                 150                 155                 160

Ala Arg Arg Leu Ile Ala Asp Leu Gly Ser Thr Ser Ile Thr Asn Leu
                165                 170                 175

Gly Phe Arg Asp Asn Trp Val Phe Cys Gly Gly Lys Gly Ile Lys Thr
                180                 185                 190

Lys Ser Pro Phe Glu Gln His Ile Lys Asn Asn Lys Asp Thr Asn Lys
                195                 200                 205

Tyr Glu Gly Trp Pro Glu Val Val Glu Met Glu Gly Cys Ile Pro Gln
210                 215                 220

Lys Gln Asp
225
```